United States Patent [19]

Suzuki et al.

[11] Patent Number: 5,405,944

[45] Date of Patent: Apr. 11, 1995

[54] GLYCOSIDES OF CATECHOL ESTROGENS

[75] Inventors: Takehiko Suzuki, Kasugai; Sadaaki Komura, Kani; Naoko Ishida, Tajimi; Nobuko Ohishi, Inuyama; Kunio Yagi, Aichi, all of Japan

[73] Assignee: Institute of Applied Biochemistry, Gifu, Japan

[21] Appl. No.: 950,512

[22] Filed: Sep. 25, 1992

[30] Foreign Application Priority Data

Oct. 1, 1991 [JP] Japan .................. 3-278973
Oct. 15, 1991 [JP] Japan .................. 3-293801
Oct. 15, 1991 [JP] Japan .................. 3-293802
Oct. 24, 1991 [JP] Japan .................. 3-303874
Apr. 20, 1992 [JP] Japan .................. 4-125471
Apr. 20, 1992 [JP] Japan .................. 4-125472

[51] Int. Cl.$^6$ .................. A61K 37/14; A61K 31/595; A61K 31/58
[52] U.S. Cl. ..................... 536/5; 536/1.11; 552/502; 552/623; 552/624
[58] Field of Search ............... 536/5, 1.11; 514/172, 514/26, 171; 552/502, 623, 624

[56] References Cited

PUBLICATIONS

J. Clin. Biochem Nutr., vol. 3, pp. 233-240, 1987.
Journal of Clinical Endocrinology and Metabolism, vol. 54, pp. 150-154, 1982.
J. Chem. Soc., vol. 80, pp. 1213-1216, 1958.
Tetrahedron, vol. 10, pp. 144-147, 1960.
J. Am. Chem. Soc., vol. 25, pp. 144-147, 1960.
Chem. Pharm, Bull., vol. 20, pp. 1842-1843, 1972.
Steroids, XXIII, pp. 287-290, 1973.
Steroids, vol. 21, pp. 205-218, 1972.
Steroids, vol. 28, No. 5, pp. 733-741, 1976.
Steroids, vol. 40, No. 4, pp. 389-392, 1982.
Chem. Pharm. Bull., vol. 18, pp. 474-480, 1191-1195, 1970.
Chem. Pharm. Bull., vol. 36, pp. 419-423, 1988.

Primary Examiner—David M. Naff
Assistant Examiner—L. Blaine Lankford
Attorney, Agent, or Firm—Nikaido, Marmelstein, Murray & Oram

[57] ABSTRACT

There are described novel glycosides of catechol estrogen, a method of preparing the same, and a medicament comprising one of the glycosides as an active ingredient. The glycosides are shown by the formula of

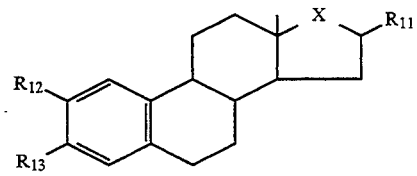

wherein X is carbonyl group or

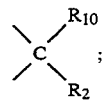

$R_{10}$ is hydroxyl group or glycosyloxy group, and $R_2$ is a hydrogen atom or ethynyl group; $R_{11}$ is a hydrogen atom, hydroxyl group, or glycosyloxy group; $R_{12}$ is hydroxyl group or glycosyloxy group; and $R_{13}$ is hydroxyl group or glycosyloxy group, in which glycosyloxy group is selected from the group consisting of glucosyloxy, galactosyloxy, mannosyloxy, arabinosyloxy, ribosyloxy, xylosyloxy, fructosyloxy, rhamnosyloxy, fucosyloxy, maltosyloxy, cellobiosyloxy, lactosyloxy, sucrosyloxy, maltotriosyloxy, maltotetraosyloxy, maltopentaosyloxy, maltohexaosyloxy, maltoheptaosyloxy, and sialosyloxy, and in this case, at least one of $R_{10}$, $R_{11}$, $R_{12}$, and $R_{13}$ is glycosyloxy group as defined above.

2 Claims, No Drawings

GLYCOSIDES OF CATECHOL ESTROGENS

BACKGROUND OF THE INVENTION

1. Field of the Invention

The present invention relates to novel glycosides of catechol estrogens, a process for the manufacture thereof, and a medicament comprising at least one of the glycosides for the prevention and treatment of lipid peroxide- and free radical-related diseases.

2. Related Arts

It is known that lipid peroxides are causative of ischemia-reperfusion injury, ischemic heart disease, atherosclerosis, retinopathy in infant, siderosis, cataract, hepatitis, pancreatitis, diabetic microangiopathy, melanoderma, liver spots, pre-eclampsia and aging itself. Therefore, the prevention of lipid peroxidation by use of suitable antioxidants is beneficial for the prophylactic and treatment of such diseases. Thus, it is in need to develop effective antioxidants as medical compound. In 1987, Yoshino et al. reported that estrogens and their metabolites catechol estrogens are effective to prevent an increase in lipid peroxide levels in mice [K. Yoshino et al., "J. Clin. Biochem. Nutr.", Vol. 3, pages 233–240 (1987)].

Thus, estrogens and catechol estrogens were thought to be hopeful for clinical application, however, the following disadvantages thereof make it difficult: Since these compounds are scarcely soluble in water, it is difficult to prepare an injection. Estrogens are not applicable to men because of their activity as a female hormone. Although estrogenic activity of catechol estrogens is almost nil, they are unstable against exposure to air and light so that the development of a medicament comprising catechol estrogen is not progressing. In addition, it is known that a half life of catechol estrogens in human blood is very short due to high susceptibility to be taken up into red blood cells and to be metabolized by catechol-O-methyl-transferase in the cells. Accordingly, these characteristics of catechol estrogens make it difficult to develop useful medicaments, even though they have a potent antioxidant activity.

As to organic synthesis of catechol estrogens, not a few papers were reported in literatures as listed below:

(a) J. Fishman, "J. Am. Chem. Soc.", 80, 1213 (1958),
(b) P. N. Rao, et al., "Tetrahedron", 10, 144 (1960),
(c) J. Fishman, "J. Org. Chem.", 25, 585 (1960),
(d) T. Nambara, et al., "Chem. Pharm. Bull.", 18, 474 (1970),
(e) T. Nambara, et al., "Chem. Pharm. Bull.", 18, 1191 (1970),
(f) I. Yoshizawa, et al., "Chem. Pharm. Bull.", 20, 1842 (1972),
(g) K. Kovacs, et al., "Acta Phys. Chem.", 19, 287 (1973),
(h) H. G. Gelbke, et al., "Steroids", 21, 205 (1973),
(i) G. Stubenrauch, et al., "Steroids", 28, 733 (1976),
(j) R. G. Xie, et al., "Steroids", 40, 389 (1982), and
(k) T. Ohkubo, et al., "Chem. Pharm. Bull.", 36, 419 (1988), Among the methods previously available, only two methods gave a relatively good yield of 50 to 60% for the preparation of catechol estrogens. Namely, the method described in Reference (j) includes the Friedel-Crafts reaction of estradiol to form 2-acetylestradiol 17-acetate (yield: 57.3%) followed by the Dakin reaction at pH 8.2–8.5 to form 2-hydroxyestradiol 17-acetate (yield: 85.2%). In this case, the overall yield was 49%. According to the method described in Reference (f), estradiol was reacted with benzoyl peroxide to form 2-hydroxyestradiol 2-monobenzoate and followed by hydrolysis to give 2-hydroxyestradiol. The overall yield in this process was 60%.

When derivatives of catechol estrogens are synthesized, it is important to prepare desirable intermediates thereof, wherein a suitable protective group is introduced into desired position. For example, Nambara et al. [References (d) and (e)] described the preparation of 2-acetoxyestrogens 3-alkyl ether and 3-acetoxy-2-alkoxy-1,3,5(10)-estratriene compounds from corresponding acetyl estrogens by Baeyer-Villiger oxidation in yields of 65–75% and 56–60%, respectively, in order to introduce desired substitution into desired positions.

For the preparation of 2-hydroxyestrogen 3-glycoside, 2-benzyloxyestrogen is an important intermediate. The procedure described in References (d) and (e) involved 11 reaction steps for the synthesis of 2-benzyloxyestradiol 17-acetate from 3-deoxyestradiol acetate and its overall yield was only 6%, then, 2-benzyloxyestradiol 17-acetate was further subjected to glucuronidation to form 2-hydroxyestradiol 3-glucuronide in a overall yield of 0.33%.

Thus, the procedures previously reported are not suitable for the manufacture thereof, because starting material is expensive, the process involves many reaction steps, and yield is not satisfactory.

SUMMARY OF THE INVENTION

An object of the invention is to provide novel glycosides of catechol estrogens which have an effective antioxidant activity, high solubility in water, and sufficient stability in body fluid and during the process of manufacture thereof.

Another object of the invention is to provide suitable processes for the manufacture of catechol estrogen compounds, by taking the following points into consideration:

(a) The starting material is available at reasonable cost;
(b) The number of reaction steps is minimum;
(c) Reaction time is as short as possible, and
(d) Yield is satisfactory.

The present inventors energetically studied and investigated to find a simple process for preparing 2-acetylestrogens with a good yield, from which they successfully prepared various glycosylated compounds of catechol estrogens. The glycosylated compounds thus obtained were met to their needs mentioned above.

The process according to the invention is shown in the following Scheme.

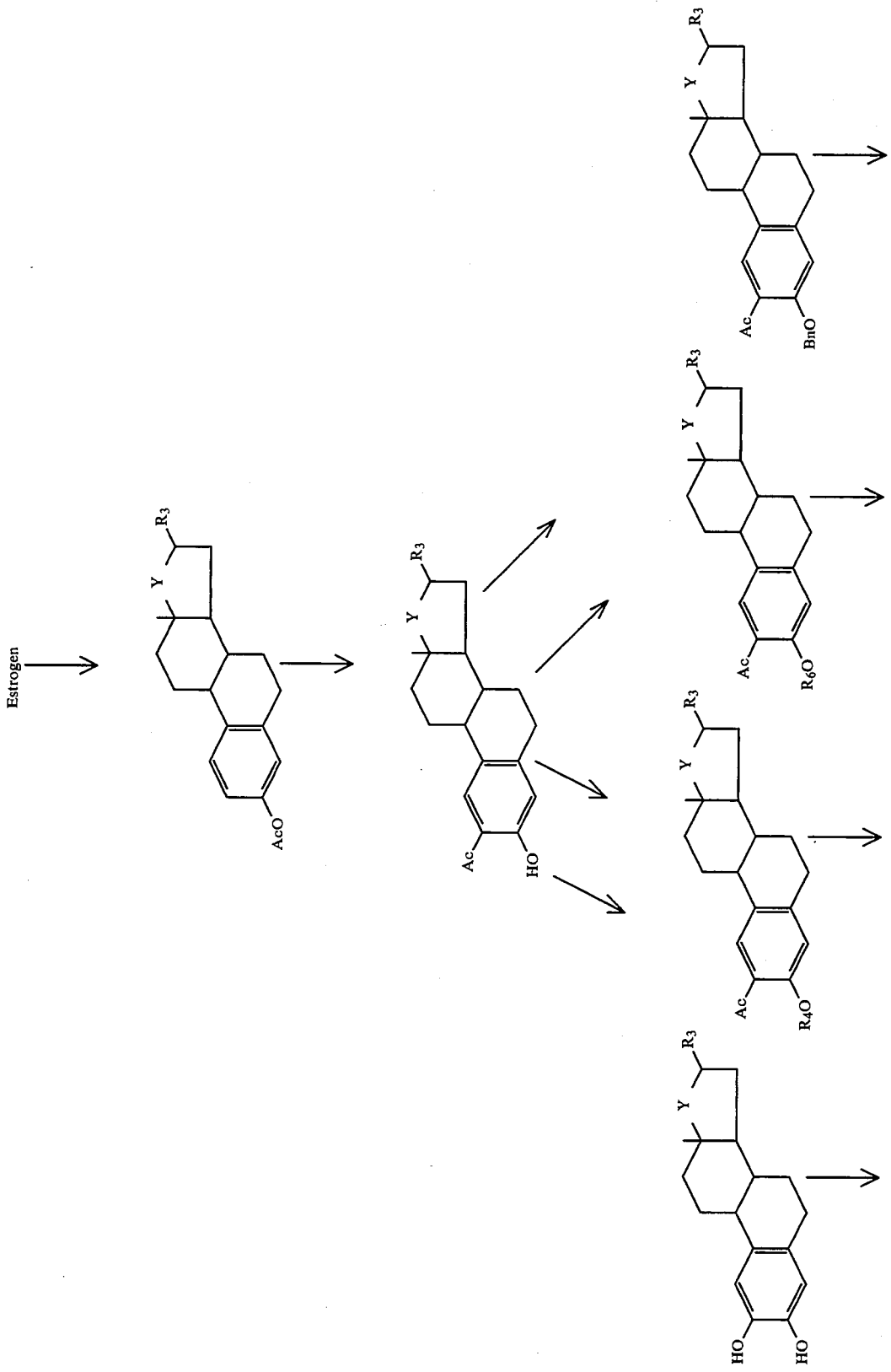

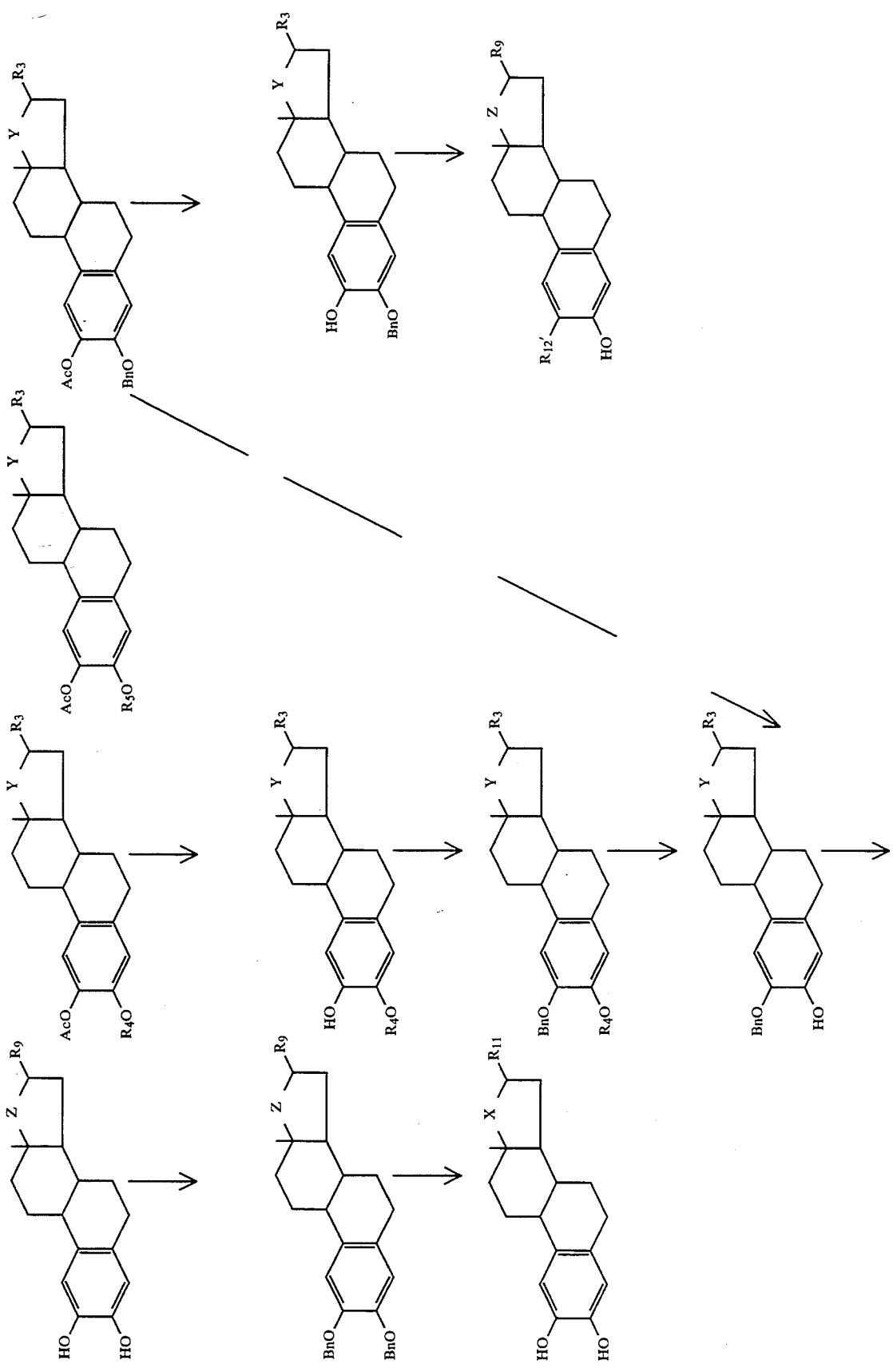

-continued
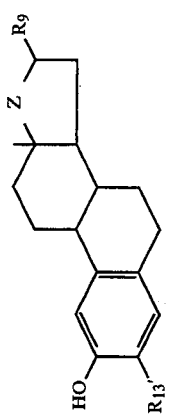

In the Scheme, Bn is benzyl group; X is carbonyl group or

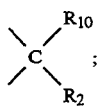

Y is carbonyl group or

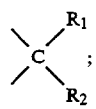

Z is carbonyl group or

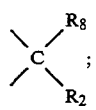

$R_1$ is acetoxyl group; $R_2$ is a hydrogen atom, or ethynyl group; $R_3$ is a hydrogen atom or acetoxyl group; $R_4$ is a protective group with an acetal type; $R_6$ is glycosyl group whose functional groups are protected; $R_8$ is hydroxyl group; $R_9$ is a hydrogen atom or hydroxyl group; $R_{10}$ is hydroxyl group or glycosyloxy group; $R_{11}$ is a hydrogen atom, hydroxyl group or glycosyloxy group; however $R_{10}$ and/or $R_{11}$ is glycosyloxy group; $R_{12'}$ is glycosyloxy group; and $R_{13'}$ is glycosyloxy group; wherein glycosyloxy group is selected from the group consisting of glucosyloxy, galactosyloxy, mannosyloxy, arabinosyloxy, ribosyloxy, xylosyloxy, fructosyloxy, rhamnosyloxy, fucosyloxy, maltosyloxy, cellobiosyloxy, lactosyloxy, sucrosyloxy, maltotriosyloxy, maltotetraosyloxy, maltopentaosyloxy, maltohexaosyloxy, maltoheptaosyloxy, and sialosyloxy.

As a result, it was found that 2-acetylestrogens of the formula:

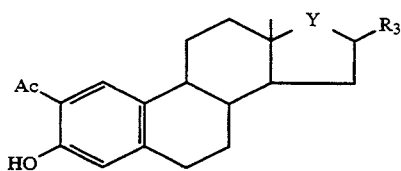

wherein Y and $R_3$ have the meanings as defined above, are useful as intermediates for the synthesis of catechol estrogens and glycosides thereof to open the way for the present invention.

The following section describes the method of the invention in detail. 2-Acetylestrogens, which are key intermediates in the present invention, can be synthesized by subjecting estrogen 3-acetate to Fries rearrangement reaction. The important point in this process is that the reaction is carried out in the presence of acetyl chloride. It was found that the yield of 2-acetylestrogen from the starting material was increased to over 80% in the presence of acetyl chloride. The preferable amount of acetyl chloride is in a range of 0.1 to 0.6 in terms of molar ratio to estrogen 3-acetate.

The synthesis of 16- and/or 17-glycosylated catechol estrogens is carried out via catechol estrogens that is prepared from 2-acetylestrogens by Dakin reaction. The previously reported Dakin reaction was carried out at pH below 9, so that the reaction took long period of time. On the contrary, the present invention found that reaction time could be lessened and yield of the product was increased to over 90% when Dakin reaction was carried out at pH 11–13.

2-Acetylestrogens are subjected to Baeyer-Villiger oxidation reaction to obtain 2-acetoxyestrogens. The previously available Baeyer-Villiger oxidation was carried out in the absence of an alkali metal salt, requiring long time to complete the reaction. On the contrary, the present invention found that Baeyer-Villiger oxidation in the presence of the alkali metal salt required only 1 or 2 days to complete the reaction by >80% yield. Alkali metal salt available in the present invention is selected from the followings; disodium hydrogen phosphate, dipotassium hydrogen phosphate, sodium hydrogen carbonate, and potassium hydrogen carbonate. Any amount of the alkali metal salt is useful and its preferable amount is in a range between 0.1 and 5 in terms of molar ratio to 2-acetylestrogens. As to protective groups for hydroxyl group at C-3 position during Baeyer-Villiger oxidation, any radical can be used such as methyl, benzyl, t-butyldimethylsilyl, triisopropylsilyl, acetyl, benzoyl, methoxymethyl, tetrahydropyranyl, and so on.

A process for preparing 3-glycosides of catechol estrogens involves 2-benzyloxyestrogens as an intermediate compound. It is prerequisite that the protection of hydroxyl group at C-3 must be stable during Baeyer-Villiger oxidation, hydrolysis of acetyl group, and benzylation. It was found that protective groups having an acetal type such as methoxymethyl, 2-methoxyethoxymethyl, and tetrahydropyranyl groups are satisfactory in this point of view. 2-Benzyloxyestrogens can be synthesized as follows: The hydroxyl group at C-3 of 2-acetylestrogens is protected by an acetal group to form 2-acetylestrogen 3-acetal compounds, subjecting to Baeyer-Villiger oxidation to form 2-acetoxyestrogen 3-acetal compounds, subjecting to hydrolysis to form 2-hydroxyestrogen 3-acetal compounds, subjecting to benzylation to form 2-benzyloxyestrogen 3-acetal compounds, and followed by elimination of 3-acetal group. According to the method of this invention, 2-benzyloxyestrogens can be synthesized from estrogens by 70% yield.

This invention also provides a short process for the preparation of 3-glycosides of catechol estrogens. That is, 2-acetylestrogen is directly glycosylated, 2-acetylestrogen 3-glycosides thus obtained are subjected to Baeyer-Villiger oxidation to form 2-acetoxyestrogen 3-glycosides, followed by hydrolysis of protective groups. According to this invention, both 2-hydroxyestrogen 3-(α-glycoside) and 2-hydroxyestrogen 3-(β-glycoside) were synthesized from estrogens by 30% yield for each.

The following section describes the process for the manufacture of catechol estrogen glycosides from estradiol as starting material. The first step is that estradiol was reacted with acetic anhydride in pyridine at room temperature for overnight, yielding estradiol diacetate stoichiometrically. Estradiol diacetate was heated at 80° C. in nitrobenzene for 1 hour in the presence of 2 mol equivalent of aluminum chloride and 0.4 mol equivalent of acetyl chloride, and then 2-acetylestradiol 17-acetate was obtained by 85% yield. 2-Acetylestradiol 17-acetate was reacted with hydrogen peroxide at room temperature for 2 hours maintaining pH in a range between 12.0 and 12.5 by the addition of sodium hydroxide and 2-hydroxyestradiol 17-acetate thus obtained was hydrolyzed by conventional method either in acidic or alkaline condition to form 2-hydroxyestradiol by overall yield of 77%.

The catechol moiety of 2-hydroxyestradiol was protected by benzyl group and the protected compound was reacted with acetobromoglucose in the presence of silver carbonate, followed by elimination of protective groups and desired 2-hydroxyestradiol 17-glucoside was obtained.

2-Acetylestradiol 17-acetate was reacted with chloromethyl methyl ether in tetrahydrofuran containing sodium hydrogen, yielding 2-acetylestradiol 17-acetate 3-methoxymethyl ether stoichiometrically, subjecting to Baeyer-Villiger oxidation with m-chloroperbenzoic acid in chloroform containing disodium hydrogen phosphate, and thus 2-acetoxyestradiol 17-acetate 3-methoxymethyl ether was formed by 88% yield.

As to the use of 2-acetoxyestradiol 17-acetate 3-methoxymethyl ether in a process of the 2-benzyloxyestradiol 17-acetate production, a few procedures can be useful. First, 2-acetatoxyestradiol 17-acetate 3-methoxymethyl ether was converted to 2-hydroxyestradiol 17-acetate 3-methoxymethyl ether by the reaction with potassium hydrogen carbonate in a mixture of acetone-water-methanol. 2-Hydroxyestradiol 17-acetate 3-methoxymethyl ether was reacted with benzyl chloride in ethanol in the presence of potassium carbonate, yielding a mixture of 17-acetoxy- and 17-hydroxy-2-benzyloxy compounds. The mixture of 2-benzyloxy compounds was further treated with acetic anhydride-pyridine. When phenyldiazomethane was used as a benzylating agent, acetyl group at C-17 was retained. Methoxymethyl group of 2-benzyloxyestradiol 17-acetate 3-methoxymethyl ether was eliminated to give 2-benzyloxyestradiol 17-acetate. Second, 2-acetatoxyestradiol 17-acetate 3-methoxymethyl ether was hydrolyzed in methanol in the presence of sodium hydroxide, and 2-hydroxyestradiol 3-methoxymethyl ether thus obtained was reacted with benzyl chloride in ethanol in the presence of potassium carbonate to form 2-benzyloxyestradiol 3-methoxymethyl ether. 17-Hydroxyl group of 2-benzyloxyestradiol 3-methoxymethyl ether was reacted with acetic anhydride-pyridine for acetylation, followed by elimination of methoxymethyl group to give 2-benzyloxyestradiol 17-acetate. Third, the intermediate 2-benzyloxyestradiol 3-methoxymethyl ether was subjected to hydrolysis in methanol containing HCl to form 2-benzyloxyestradiol, followed by acetylation of hydroxyl group at C-3 and C-17 in a solution containing acetic anhydride-pyridine. Then, 2-benzyloxyestradiol 17-acetate was obtained by selective hydrolysis in a mixture of acetone-water-methanol in the presence of potassium hydrogen carbonate.

These three different processes provide 2-benzyloxyestradiol 17-acetate stoichiometrically from 2-acetoxyestradiol 17-acetate 3-methoxymethyl ether. 2-Benzyloxyestradiol 17-acetate can be reacted with acetobromoglucose in the presence of $CdCO_3$ and after deprotection, 2-hydroxyestradiol 3-glucoside was obtained.

When 2-acetylestradiol 17-acetate was reacted with acetobromoglucose in toluene containing $CdCO_3$, two anomers, 2,3,4,6-tetra-O-acetyl-1-O-(2-acetyl-17$\beta$-acetoxy-1,3,5(10)-estratriene-3-yl)-$\beta$-D-glucopyranoside and 2,3,4,6-tetra-O-acetyl-1-O-(2-acetyl-17$\beta$-acetoxy-1,3,5(10)-estratriene-3-yl)-$\alpha$-D-glucopyranoside, were formed by 39% and 48% yield, respectively.

Each anomer was subjected to Baeyer-Villiger oxidation in the presence of an alkali metal salt to form 2-acetoxyl compounds, followed by elimination of acetyl group under alkaline condition to form 2-hydroxyestradiol 3-($\beta$-D-glucopyranoside) or 2-hydroxyestradiol 3-($\alpha$-D-glucopyranoside) by 83% and 70% yield, respectively. Overall yield of $\beta$-anomer and $\alpha$-anomer was 28% and 29% respectively, from estradiol as starting material.

2-Acetylestradiol 17-acetate was transformed to 2-acetylestradiol 17-acetate 3-benzyl ether, subjecting to Baeyer-Villiger oxidation in the presence of an alkali metal salt to form 2-acetoxyestradiol 17-acetate 3-benzyl ether, subjecting selective hydrolysis at C-2 to form 2-hydroxyestradiol 17-acetate 3-benzyl ether. 2-Hydroxyestradiol 17-acetate 3-benzyl ether was reacted with acetobromoglucose in the presence of $CdCO_3$, and after deprotection, 2-hydroxyestradiol 2-glucoside was obtained.

The present inventors have found that novel glycosides of catechol estrogens acquired an increased hydrophilicity. For example, the volume of water required to dissolve 1 mg of various glycosides is as following; 2 to 3 ml for 17-glucoside, 2 ml for 17-maltoside, 0.7 ml for 2-glucoside, and 3 ml for 3-glucoside, while 1 mg of 2-hydroxyestradiol cannot be dissolved in 3 ml of water. Accordingly, the glycosides obtained in the present invention provide a way to prepare an injection containing the same.

It was also found that glycosides of catechol estrogens retained antioxidant activity in the same degree to that of parent catechol estrogens and that the rate of incorporation of the glycosides into red blood cells was extremely decreased, indicating that half life of the glycosides was much improved.

The glycosides of catechol estrogens obtained by the present invention have not estrogenic activity at the dosage required for antioxidant activity. The glycosides of catechol estrogens provide medicaments with desirable types such as injection, powder, tablets, capsules, ointment, and so on.

PREFERRED EMBODIMENTS OF THE INVENTION

The invention will now be further explained in more detail with reference to Manufacturing Examples, Test Examples and Medicine Preparation Examples.

EXAMPLE 1 a) Estradiol diacetate

A mixture of estradiol (30 g, 110 mmol), pyridine (300 ml, 3.71 mol) and acetic anhydride (105 ml, 1.08 mol) was stirred overnight at room temperature. The reaction mixture was poured onto ice (1500 g) and precipitate was collected by filtration, washed with water, and dried in vacuo to afford 39.3 g (100%) of the titled compound.

$^1$H-NMR spectrum (DMSO-$d_6$) $\delta$ ppm: 0.78 (3H, s, 18-$CH_3$), 1.1–2.9 (15H, m, CH and $CH_2$), 2.01 (3H, s, $C_{17}$—$OCOCH_3$), 2.23 (3H, s, $C_3$—$OCOCH_3$), 4.62 (1H, t like, $C_{17}$—H), 6.83 (2H, m, $C_2$—H and $C_4$—H), and 7.28 (1H, d, J=10 Hz, $C_1$—H).

b) 2-Acetylestradiol 17-acetate

To a solution of estradiol diacetate (25.0 g, 70.1 mmol) in nitrobenzene (250 ml), $AlCl_3$ (18.6 g, 139 mmol) and acetyl chloride (2.0 ml, 28 mmol) were added, and the solution was stirred for 1 hour at 80° C. The reaction mixture was cooled and poured onto ice (1000 g). To this solution concentrated HCl (100 ml) was added. After extraction with CHCl₃, the organic layer was washed successively with 1N-HCl, saturated NaHCO₃ solution, and brine, and concentrated in vacuo to obtain a crude product (25.3 g), to which methanol (MeOH) (150 ml) was added to afford 17.7 g (70.6%) of the titled compound as an insoluble material. The filtrate was concentrated in vacuo and subjected to silica gel chromatography (elution solvent, CHCl₃:hexane=2:1) to afford additional 3.48 g of the titled compound. The total yield was 85%.

$^1$H-NMR spectrum (CDCl₃) δ ppm: 0.84 (3H, s, 18-CH₃), 1.2–3.0 (15H, m, CH and CH₂), 2.07 (3H, s, $C_{17}$—OCOCH₃), 2.59 (3H, s, $C_2$—COCH₃), 4.70 (1H, t like, $C_{17}$—H), 6.67 (1H, s, $C_4$—H), 7.59 (1H, s, $C_1$—H), and 12.03 (1H, s, $C_3$—OH).

EXAMPLE 2

2-Hydroxyestradiol 17-acetate

To a mixture of 2-acetylestradiol 17-acetate (1.00 g, 2.81 mmol) obtained by the process described in Example 1-b, dioxane (30 ml), and water (5 ml), 30% aqueous solution of hydrogen peroxide (0.600 ml, 5.28 mmol) was added over 10 minutes and subsequently 2N-NaOH (2.3 ml, 4.6 mmol) was added dropwise over 1.5 hours during which the pH of the solution was maintained within a range of 11.0–12.5. After the reaction mixture was stirred for further 30 minutes, the pH of the solution was brought to 4.4 by addition of acetic acid (10 ml). To this solution Na₂SO₃ solution was added. After extraction with ethyl acetate (AcOEt), the organic layer was washed with brine, dried over anhydrous Na₂SO₄, and evaporated in vacuo to obtain a crude product (1.14 g), which was, in turn, subjected to silica gel chromatography (elution solvent, hexane:AcOEt=2:1) to afford 788 mg (85%) of the titled compound.

$^1$H-NMR spectrum (CDCl₃) δ ppm: 0.82 (3H, s, 18-CH₃), 1.2–2.9 (15H, m, CH and CH₂), 2.08 (3H, s, $C_{17}$—OCOCH₃), 4.75 (1H, t like, $C_{17}$—H), 5.44 (1H, s, Ar—OH), 5.97 (1H, s, Ar—OH), 6.59 (1H, s, $C_4$—H), and 6.80 (1H, s, $C_1$—H).

Silica gel TLC: Rf=0.31 (hexane:AcOEt=2:1).

EXAMPLE 3 a) 2-Hydroxyestradiol 17-acetate

To a mixture of 2-acetylestradiol 17-acetate (80.5 g, 226 mmol) obtained by the process described in Example 1-b, dioxane (2500 ml), and water (250 ml), 30% aqueous solution of hydrogen peroxide (40.3 ml, 355 mmol) was added and subsequently 2N-NaOH (193 ml, 386 mmol) was added dropwise over 1.5 hours during which the pH of the solution was maintained within a range of 12.0–12.5. After the reaction mixture was stirred for further 30 minutes, the pH of the solution was brought to 4.5 by addition of acetic acid (800 ml). To this solution Na₂SO₃ solution was added. After extraction with AcOEt, the organic layer was washed with brine, dried over anhydrous Na₂SO₄, and evaporated in vacuo to obtain a crude product (100 g) of the titled compound.

b) 2-Hydroxyestradiol

To the crude product (100 g) of 2-hydroxyestradiol 17-acetate obtained by the process described in Example 3-a, MeOH (3600 ml) and concentrated HCl (400 ml) were added, and the solution was refluxed for 1 hour. After the reaction mixture was cooled, water and AcOEt were added to it and the solution was neutralized by addition of NaHCO₃, and extracted with AcOEt. The organic layer was washed with brine, and dried over anhydrous Na₂SO₄, and then evaporated in vacuo to obtain a crude product (68.7 g), which was, in turn, subjected to silica gel chromatography (elution solvent, hexane:AcOEt=1:1) to afford 59 g (91% from 2-acetylestradiol 17-acetate) of the titled compound.

$^1$H-NMR spectrum (DMSO-d₆) δ ppm: 0.66 (3H, s, 18-CH₃), 0.8–2.7 (15H, m, CH and CH₂), 3.52 (1H, m, $C_{17}$—H), 4.48 (1H, d, J=5 Hz, $C_{17}$—OH), 6.39 (1H, s, $C_4$—H), 6.62 (1H, s, $C_1$—H), 8.42 (1H, s, Ar—OH), and 8.48 (1H, s, Ar—OH).

Silica gel TLC: Rf=0.30 (hexane:AcOEt=1:1).

MS spectrum (EI/DI) m/z: 288 (M+).

EXAMPLE 4 a) 2-Hydroxyestradiol 2,3-dibenzyl ether

To a solution of 2-hydroxyestradiol 10.0 g (37.4 mmol) obtained by the process described in Example 3-b in ethanol (EtOH, 200 ml), K₂CO₃ (12.0 g) and benzyl chloride (10.0 g) were added, and the mixture was refluxed for 5 hours. After the reaction mixture was cooled to room temperature, it was then filtered to remove an insoluble material. The insoluble material was washed with AcOEt. The filtrate and washings were combined and concentrated in vacuo to obtain a crude product, which was, in turn, subjected to silica gel chromatography (elution solvent, hexane:AcOEt=4:1) to afford 13.0 g (80.5%) of the titled compound.

$^1$H-NMR spectrum (CDCl₃) δ ppm: 0.77 (3H, s, 18-CH₃), 1.0–2.9 (15H, m, CH and CH₂), 3.72 (1H, t like, $C_{17}$—H), 5.11 (4H, s, $C_6H_5CH_2$ x 2), 6.68 (1H, s, $C_4$—H), 6.92 (1H, s, $C_1$—H), and 7.2–7.5 (10H, m, $C_6H_5$ x 2).

Silica gel TLC: Rf=0.58 (hexane:AcOEt=1:1).

b) 2,3,4,6-Tetra-O-acetyl-1-O-(2,3-dibenzyloxy-1,3,5(10)-estratriene-17β-yl)-β-D-glucopyranoside Ag₂CO₃ (471 mg, 1.71 mmol) was added to a solution of 2-hydroxyestradiol 2,3-dibenzyl ether (200 mg, 0.427 mmol) obtained by the process described in Example 4-a in benzene (20 ml), and the suspension was distilled until 10 ml of benzene had been removed over 50 minutes to remove moisture. A solution of acetobromoglucose (527 mg, 1.28 mmol) in benzene (30 ml) was added dropwise to the stirred mixture over 2 hours and an equal volume of benzene was simultaneously distilled to give a constant volume of the reaction mixture. Distillation was continued for further 1 hour, during which benzene was added dropwise to maintain the volume of the suspension. An insoluble material was removed off by filtration through a pad of Celite and washed with benzene and CH₂Cl₂. The filtrate and washings were combined and evaporated in vacuo to obtain a crude product, which was, in turn, subjected to silica gel thin-layer chromatography (developing solvent, hexane:AcOEt=2.5:1) to afford 263 mg (77.1%) of the titled compound.

$^1$H-NMR spectrum (CDCl₃) δ ppm: 0.74 (3H, s, 18-CH₃), 1.0–2.9 (15H, m, estrogen CH and CH₂), 2.01, 2.03, 2.07 and 2.09 (3H x 4, s x 4, OCOCH₃x 4), 3.63 (2H, m, $C_{17}$—H and pyranose $C_5$—H), 4.0–4.4 (2H, m, pyranose $C_6$—H₂), 4.56 (1H, d, J=8 Hz, pyranose $C_1$—H), 4.8–5.3 (3H, m, pyranose $C_2$—H, $C_3$—H and $C_4$—H), 5.11 (4H, s, $C_6H_5CH_2$ x 2), 6.67 (1H, s, Ar $C_4$—H), 6.89 (1H, s, Ar $C_1$—H), and 7.1–7.6 (10H, m, $C_6H_5$ x 2).

IR spectrum (KBr) cm$^{-1}$: 2924, 1756, 1504, 1452, 1368, 1222, 1036, 736, and 698.

MS spectrum (EI/DI) m/z: 798 (M+).

Silica gel TLC: Rf=0.37 (hexane:AcOEt=2:1).

c) 1-O-(2,3-Dibenzyloxy-1,3,5(10)-estratriene-17β-yl)-β-D-glucopyranoside

To 2,3,4,6-tetra-O-acetyl-1-O-(2,3-dibenzyloxy-1,3,5(10)-estratriene-17β-yl)-β-D-glucopyranoside (1.04 g, 1.30 mmol) obtained by the process described in Example 4-b, MeOH (73 ml) was added. After the mixture was mildly heated to obtain a homogeneous solution, 1N-NaOH (30 ml) was added, and the mixture was stirred for 3 hours. After removal of MeOH by evaporation, the residue was extracted with AcOEt. The organic layer was washed with brine, dried over anhydrous Na$_2$SO$_4$, and then concentrated in vacuo to obtain a crude product (865 mg), which was, in turn, subjected to silica gel chromatography (elution solvent, CHCl$_3$:MeOH=10:1) to afford 613 mg (74.7%) of the titled compound.

$^1$H-NMR spectrum (CD$_3$OD) δ ppm: 0.83 (3H, s, 18-CH$_3$), 1.0–2.8 (15H, m, estrogen CH and CH$_2$), 3.1–4.0 (7H, m, C$_{17}$—H and pyranose CH—O— and CH$_2$—O—), 4.35 (1H, d, J=8 Hz, pyranose C$_1$—H), 5.01 (4H, s, C$_6$H$_5$CH$_2$ x 2), 6.65 (1H, s, Ar C$_4$—H), 6.86 (1H, s, Ar C$_1$—H), and 7.2–7.4 (10H, m, C$_6$H$_5$ x 2).

IR spectrum (KBr) cm$^{-1}$: 3420, 2920, 1502, 1452, 1262, 1074, 1014, 734, and 696.

MS spectrum (FAB, positive): 630 (M+).

Silica gel TLC: Rf=0.28 (CHCl$_3$:MeOH=10:1).

d) 2-Hydroxyestradiol 17-(β-D-glucopyranoside)

To a solution of 1-O-(2,3-dibenzyloxy-1,3,5(10)-estratriene-17β-yl)-β-D-glucopyranoside (1.89 g, 3.00 mmol) obtained by the process described in Example 4-c in MeOH (150 ml), a suspension of 5% Pd/C (200 mg) in MeOH (200 ml) was added, and the mixture was stirred under bubbling of H$_2$ for 20 hours. The catalyst Pd/C was removed off by filtration through a pad of Celite. The filtrate was evaporated in vacuo to obtain a crude product (1.39 g), which was, in turn, subjected to silica gel chromatography (elution solvent, CHCl$_3$:MeOH=8:1) to afford 1.21 g (89.7%) of the titled compound.

$^1$H-NMR spectrum (CD$_3$OD) δ ppm: 0.86 (3H, s, 18-CH$_3$), 1.0–2.8 (15H, m, estrogen CH and CH$_2$), 3.0–4.0 (7H, m, C$_{17}$—H and pyranose CH—O— and CH$_2$—O—), 4.37 (1H, d, J=8 Hz, pyranose C$_1$—H), 6.44 (1H, s, Ar C$_4$—H), and 6.69 (1H, s, Ar C$_1$—H).

$^{13}$C-NMR spectrum (DMSO-d$_6$) δ ppm: 11.38, 22.54, 26.11, 27.04, 28.34, 28.50, 37.06, 38.36, 42.91, 43.45, 49.36, 61.06, 70.11, 73.63, 76.69, 76.77, 86.91, 103.00, 112.42, 115.15, 126.35, 130.36, and 142.76.

IR spectrum (KBr) cm$^{-1}$: 3376, 2920, 1514, 1450, 1354, 1276, 1076, and 1018.

MS spectrum (FAB, positive): 450 (M+).

Silica gel TLC: Rf=0.54 (CHCl$_3$:MeOH=3:1).

Solubility: 1.0 mg/2–3 ml (H$_2$O).

EXAMPLE 5 a) 2,3,6,2',3',4',6'-Hepta-O-acetyl-1-O-(2,3-dibenzyloxy-1,3,5(10)-estratriene-17β-yl)-β-maltoside Ag$_2$CO$_3$ (7.07 g, 25.6 mmol) was added to a solution of 2-hydroxyestradiol 2,3-dibenzyl ether (3.00 g, 6.40 mmol) obtained by the process described in Example 4-a in benzene (300 ml), and the suspension was distilled until 160 ml of benzene had been removed over 1 hour to remove moisture. A solution of acetobromomaltose (13.4 g, 19.2 mmol) in benzene (300 ml) was added dropwise to the stirred mixture over 1.5 hours and an equal volume of benzene was simultaneously distilled to give a constant volume of the reaction mixture. Distillation was continued for further 1 hour, during which benzene was added dropwise to maintain the volume of the suspension. An insoluble material was removed off by filtration through a pad of Celite and washed with benzene. The filtrate and washings were combined and evaporated in vacuo to obtain a crude product, which was, in turn, subjected to silica gel chromatography (elution solvent, hexane:AcOEt=1.5:1) to afford 4.22 g (60.7%) of the titled compound.

$^1$H-NMR spectrum (CDCl$_3$) δ ppm: 0.72 (3H, s, 18-CH$_3$), 0.9–2.9 (36H, m, estrogen CH and CH$_2$, and OCOCH$_3$ x 7), 4.58 (1H, d, J=8 Hz, pyranose C$_1$—H), 3.5–4.5 and 4.7–5.6 (14H, m, C$_{17}$—H, and pyranose CH—O— and CH$_2$—O—), 5.11 (4H, s, C$_6$H$_5$CH$_2$ x 2), 6.67 (1H, s, Ar C$_4$—H), 6.89 (1H, s, Ar C$_1$—H), and 7.2–7.6 (10H, m, C$_6$H$_5$ x 2).

IR spectrum (KBr) cm$^{-1}$: 2928, 1754, 1504, 1370, 1230, 1032, 736, and 698.

MS spectrum (EI/DI) m/z: 1086 (M+).

Silica gel TLC: Rf=0.45 (hexane:AcOEt=1:1).

b) 1-O-(2,3-Dibenzyloxy-1,3,5(10)-estratriene-17β-yl)-β-maltoside

To 2,3,6,2',3',4',6'-hepta-O-acetyl-1-O-(2,3-dibenzyloxy-1,3,5(10)-estratriene-17β-yl)-β-maltoside (3.87 g, 3.56 mmol) obtained by the process described in Example 5-a, MeOH (300 ml) was added. After the mixture was mildly heated to obtain a homogeneous solution, 1N-NaOH (100 ml) was added to it, and the mixture was stirred at room temperature for 1 hour. After removal of MeOH by evaporation, the residue was extracted with CHCl$_3$. The organic layer was washed with brine, and dried over anhydrous Na$_2$SO$_4$, and then concentrated in vacuo to obtain a crude product (3.81 g), which was, in turn, subjected to silica gel chromatography (elution solvent, CHCl$_3$:MeOH=5:1) to afford 1.75 g (62.1%) of the titled compound.

$^1$H-NMR spectrum (CD$_3$OD) δ ppm: 0.81 (3H, s, 18-CH$_3$), 0.9–2.8 (15H, m, estrogen CH and CH$_2$), 3.1–4.1 (13H, m, C$_{17}$—H, and pyranose CH—O— and CH$_2$—O—), 4.33 (1H, d, J=8 Hz, pyranose C$_1$—H), 4.93 (4H, br.s, C$_6$H$_5$CH$_2$ x 2), 5.19 (1H, d, J=3 Hz, pyranose C$_{1'}$—H), 6.58 (1H, s, Ar C$_4$—H), 6.80 (1H, s, Ar C$_1$—H), and 7.0–7.5 (10H, m, C$_6$H$_5$ x 2).

IR spectrum (KBr) cm$^{-1}$: 3396, 2920, 1502, 1452, 1260, 1020, 736, and 696.

MS spectrum (FAB, positive): 792 (M+).

Silica gel TLC: Rf=0.26 (CHCl$_3$:MeOH=5:1).

c) 2-Hydroxyestradiol 17-(β-maltoside)

To a solution of 1-O-(2,3-dibenzyloxy-1,3,5(10)-estratriene-17β-yl)-β-maltoside (1.66 g, 2.09 mmol) obtained by the process described in Example 5-b in MeOH (160 ml), 5% Pd/C (850 mg) was added, and the mixture was stirred under bubbling of H$_2$ for 7 hours. The catalyst Pd/C was removed off by filtration through a pad of Celite. The filtrate was evaporated in vacuo to obtain a crude product (1.18 g). After the crude product was dissolved in hot MeOH (20 ml), hot CHCl$_3$ (40 ml) was added to this solution and an insoluble material was removed off by filtration. To the resulting filtrate, CHCl$_3$ (100 ml) was added, and the precipitated white solid was collected by filtration and dried in vacuo to afford 711 mg (55.5%) of the titled compound.

$^1$H-NMR spectrum (CD$_3$OD) δ ppm: 0.86 (3H, s, 18-CH$_3$), 1.0–2.8 (15H, m, estrogen CH and CH$_2$), 3.1–4.1 (13H, m, C$_{17}$—H, and pyranose CH—O— and CH$_2$—O—), 4.38 (1H, d, J=8 Hz, pyranose C$_1$—H), 5.17 (1H, d, J=3 Hz, pyranose C$_{1'}$—H), 6.45 (1H, s, Ar C$_4$—H), and 6.69 (1H, s, Ar C$_1$—H).

$^{13}$C-NMR spectrum (DMSO-d$_6$) δ ppm: 11.32, 22.43, 26.17, 27.04, 28.28, 28.39, 37.01, 38.52, 42.91, 43.40, 49.30, 60.74, 69.89, 72.39, 73.25, 75.09, 76.50, 79.05, 79.59, 87.01, 100.61, 102.84, 112.42, 115.51, 126.24, 130.30, and 142.82.

IR spectrum (KBr) cm$^{-1}$: 3376, 2920, 1514, 1450, 1354, 1274, and 1028.

MS spectrum (FAB, positive): 635 (M$^+$ +Na).

Reverse phase TLC: Rf=0.41 (MeOH: H$_2$O=3:2).

Solubility: 1.0 mg/2 ml (H$_2$O).

EXAMPLE 6 a) 2-Acetylestradiol 17-acetate 3-methoxymethyl ether

NaH (about 60% oil suspension, 1.01 g) was washed with hexane by 3 times, and tetrahydrofuran (THF, 40 ml) was added. Chloromethyl methyl ether (3.83 ml, 50.4 mmol), and 2-acetylestradiol 17-acetate (6.00 g, 16.8 mmol) obtained by the process described in Example 1-b in THF (70 ml) were added to the NaH suspension. After the mixture was stirred at 50° C. for 20 minutes, it was poured onto ice (100 g). Water (600 ml) was added to the mixture. The precipitate was collected by filtration, washed with water, and then dried in vacuo to afford 6.76 g (100%) of the titled compound.

$^1$H-NMR spectrum (CDCl$_3$) δ ppm: 0.82 (3H, s, 18-CH$_3$), 1.2–3.0 (15H, m, estrogen CH and CH$_2$), 2.05 (3H, s, C$_{17}$—OCOCH$_3$), 2.62 (3H, s, C$_2$—COCH$_3$), 3.50 (3H, s, O—CH$_3$), 4.68 (1H, t like, C$_{17}$—H), 5.24 (2H, s, O—CH$_2$—O), 6.88 (1H, s, Ar C$_4$—H), and 7.66 (1H, s, Ar C$_1$—H).

Silica gel TLC: Rf=0.32 (hexane:AcOEt=4:1).

b) 2-Hydroxyestradiol 2,17-diacetate 3-methoxymethyl ether

A mixture of 2-acetylestradiol 17-acetate 3-methoxymethyl ether (2.50 g, 6.24 mmol) obtained by the process described in Example 6-a, m-chloroperbenzoic acid (2.15 g, 12.5 mmol), Na$_2$HPO$_4$ (1.77 g, 12.5 mmol), and CHCl$_3$ (50 ml) was stirred at room temperature for 16 hours. After removed an insoluble material by filtration, the filtrate was poured into ice-cooled ether. The organic layer was washed successively with 5% Na$_2$CO$_3$ solution, water, and brine, thereafter dried over anhydrous Na$_2$SO$_4$, and evaporated in vacuo to obtain a crude product (2.90 g). A part (1.80 g) of the crude product was, in turn, subjected to silica gel chromatography (elution solvent, hexane:AcOEt=4:1) to afford 1.41 g (87.6%) of the titled compound.

$^1$H-NMR spectrum (CDCl$_3$) δ ppm: 0.81 (3H, s, 18-CH$_3$), 1.2–3.0 (15H, m, estrogen CH and CH$_2$), 2.05 (3H, s, C$_{17}$—OCOCH$_3$), 2.30 (3H, s, C$_2$—OCOCH$_3$), 3.46 (3H, s, O—CH$_3$), 4.69 (1H, t like, C$_{17}$—H), 5.12 (2H, s, O—CH$_2$—O), 6.90 (1H, s, Ar C$_4$—H), and 6.93 (1H, s, Ar C$_1$—H).

Silica gel TLC: Rf=0.36 (hexane:AcOEt=4:1).

EXAMPLE 7 a) 2-Acetylestradiol 17-acetate 3-benzyl ether

To a solution of 2-acetylestradiol 17-acetate (15.0 g, 42.1 mmol) obtained by the process described in Example 1-b in EtOH (200 ml), K$_2$CO$_3$ (8.73 g) and benzyl chloride (7.27 ml) were added, and the mixture was refluxed for 3 hours. Additional amounts of K$_2$CO$_3$ (5.82 g) and benzyl chloride (4.84 ml) were added, and the mixture was refluxed for further 1.5 hours. After the reaction mixture was cooled to room temperature, it was then filtered to remove an insoluble material. The filtrate was concentrated in vacuo and a residue was dissolved in CHCl$_3$ (500 ml). The CHCl$_3$ solution was washed with brine, dried over anhydrous Na$_2$SO$_4$, and then evaporated in vacuo to afford an oily residue.

A mixture of the oily residue obtained above, pyridine (150 ml), and acetic anhydride (55 ml) was stirred overnight at room temperature. The reaction mixture was poured onto ice (1500 g), and the precipitate was collected by filtration, washed with water, and then dried in vacuo to afford 18.7 g (99.6%) of the titled compound.

$^1$H-NMR spectrum (CDCl$_3$) δ ppm: 0.82 (3H, s, 18-CH$_3$), 1.1–3.0 (15H, m, CH and CH$_2$), 2.05 (3H, s, C$_{17}$—OCOCH$_3$), 2.57 (3H, s, C$_2$—COCH$_3$), 4.69 (1H, t like, C$_{17}$—H), 5.11 (2H, s, C$_6$H$_5$CH$_2$), 6.74 (1H, s, C$_4$—H), 7.39 (5H, m, C$_6$H$_5$), and 7.71 (1H, s, C$_1$—H).

Silica gel TLC: Rf=0.33 (hexane:AcOEt=5:1).

b) 2-Hydroxyestradiol 2,17-diacetate 3-benzyl ether

A mixture of 2-acetylestradiol 17-acetate 3-benzyl ether (1.00 g, 2.24 mmol) obtained by the process described in Example 7-a, m-chloroperbenzoic acid (0.773 g, 4.48 mmol), Na$_2$HPO$_4$ (0.318 g, 2.24 mmol), and CHCl$_3$ (25 ml) was stirred at room temperature for 20 hours. The reaction mixture was poured into ether (150 ml). The organic layer was washed successively with 5% NaOH solution, water, and brine, thereafter it was dried over anhydrous Na$_2$SO$_4$ and evaporated in vacuo to obtain a crude product (1.02 g), which was, in turn, subjected to silica gel chromatography (elution solvent, CHCl$_3$) to afford 838 mg (81%) of the titled compound.

$^1$H-NMR spectrum (CDCl$_3$) δ ppm: 0.82 (3H, s, 18-CH$_3$), 1.1–3.0 (15H, m, CH and CH$_2$), 2.05 (3H, s, C$_{17}$—OCOCH$_3$), 2.25 (3H, s, C$_2$—OCOCH$_3$), 4.68 (1H, t like, C$_{17}$—H), 5.04 (2H, s, C$_6$H$_5$CH$_2$), 6.71 (1H, s, C$_4$—H), 6.95 (1H, s, C$_1$—H), and 7.36 (5H, br.s, C$_6$H$_5$).

Silica gel TLC: Rf=0.49 (CHCl$_3$).

EXAMPLE 8 a) 2-Acetylestradiol 17-acetate 3-t-butyldimethylsilyl ether

A mixture of 2-acetylestradiol 17-acetate (5.00 g, 14.0 mmol) obtained by the process described in Example 1-b, t-butyldimethylsilyl chloride (3.18 g, 21.1 mmol), imidazole (2.87 g, 42.2 mmol), and dimethylformamide (30 ml) was stirred at room temperature for 20 hours. The reaction mixture was poured into water and extracted with CHCl$_3$. The organic layer was washed with brine, dried over anhydrous Na$_2$SO$_4$, and then evaporated in vacuo to obtain a crude product, which was, in turn, subjected to silica gel chromatography (elution solvent, CHCl$_3$) to afford 6.64 g (101%) of the titled compound.

$^1$H-NMR spectrum (CDCl$_3$) δ ppm: 0.25 [6H, s, Si(CH$_3$)$_2$], 0.83 (3H, s, 18-CH$_3$), 1.00 (9H, s, Si-t-C$_4$H$_9$), 1.1–3.0 (15H, m, estrogen CH and CH$_2$), 2.05 (3H, s, C$_{17}$—OCOCH$_3$), 2.58 (3H, s, C$_2$—COCH$_3$), 4.68 (1H, t like, C$_{17}$—H), 6.57 (1H, s, Ar C$_4$—H), and 7.55 (1H, s, Ar C$_1$—H).

Silica gel TLC: Rf=0.39 (CHCl$_3$).

b) 2-Hydroxyestradiol 2,17-diacetate 3-t-butyldimethylsilyl ether

A mixture of 2-acetylestradiol 17-acetate 3-t-butyldimethylsilyl ether (1.00 g, 2.12 mmol) obtained by the process described in Example 8-a, m-chloroperbenzoic acid (0.733 g, 4.25 mmol), Na$_2$HPO$_4$ (0.602 g, 4.24 mmol), and CHCl$_3$ (25 ml) was stirred at room temperature for 19 hours. The reaction mixture was poured into ether (300 ml). The organic layer was washed successively with 5% Na$_2$CO$_3$ solution, water, and brine, thereafter it was dried over anhydrous Na$_2$SO$_4$ and evaporated in vacuo to obtain a crude product, which was, in turn, subjected to silica gel chromatography (elution solvent, CHCl$_3$) to afford 898 mg (87%) of the titled compound.

$^1$H-NMR spectrum (CDCl$_3$) δ ppm: 0.19 [6H, s, Si(CH$_3$)$_2$], 0.82 (3H, s, 18-CH$_3$), 0.98 (9H, s, Si-t-C$_4$H$_9$), 1.2–2.9 (15H, m, estrogen CH and CH$_2$), 2.05 (3H, s, C$_{17}$—OCOCH$_3$), 2.26 (3H, s, C$_2$—OCOCH$_3$), 4.68 (1H, t like, C$_{17}$—H), 6.59 (1H, s, Ar C$_4$—H), and 6.90 (1H, s, Ar C$_1$—H).

Silica gel TLC: Rf=0.50 (CHCl$_3$).

EXAMPLE 9 a) 2-Acetylestradiol diacetate

A mixture of 2-acetylestradiol 17-acetate (1.00 g, 2.81 mmol) obtained by the process described in Example 1-b, pyridine (6ml), and acetic anhydride (3 ml) was stirred overnight at room temperature. The reaction mixture was poured onto ice (50 g), and the precipitate was collected by filtration, washed with water, and then dried in vacuo to afford 1.11 g (99.1%) of the titled compound.

$^1$H-NMR spectrum (CDCl$_3$) δ ppm: 0.84 (3H, s, 18-CH$_3$), 1.1–3.0 (15H, m, estrogen CH and CH$_2$), 2.07 (3H, s, C$_{17}$—OCOCH$_3$), 2.34 (3H, s, C$_3$—OCOCH$_3$), 2.53 (3H, s, C$_2$—COCH$_3$), 4.70 (1H, t like, C$_{17}$—H), 6.81 (1H, s, Ar C$_4$—H), and 7.74 (1H, s, Ar C$_1$—H).

Silica gel TLC: Rf=0.21 (CHCl$_3$).

b) 2-Hydroxyestradiol triacetate

A mixture of 2-acetylestradiol diacetate (100 mg, 0.251 mmol) obtained by the process described in Example 9-a, m-chloroperbenzoic acid (0.130 g, 0.753 mmol), Na$_2$HPO$_4$(71.3 mg, 0.502 mmol), and CHCl$_3$ (2 ml) was stirred at room temperature for 40 hours. The reaction mixture was poured into ether (50 ml). The organic layer was washed successively with 5% Na$_2$CO$_3$ solution, water, and brine, thereafter it was dried over anhydrous Na$_2$SO$_4$ and evaporated in vacuo to obtain a crude product, which was, in turn, subjected to silica gel thin-layer chromatography (developing solvent, CHCl$_3$:MeOH=100:1) to afford 92.9 mg (89%) of the titled compound.

$^1$H-NMR spectrum (CDCl$_3$) δ ppm: 0.82 (3H, s, 18-CH$_3$), 1.1–3.0 (15H, m, estrogen CH and CH$_2$), 2.05 (3H, s, C$_{17}$—OCOCH$_3$), 2.27 (6H, s, C$_2$—OCOCH$_3$ and C$_3$—OCOCH$_3$), 4.68 (1H, t like, C$_{17}$—H), 6.87 (1H, s, Ar C$_4$—H), and 7.05 (1H, s, Ar C$_1$—H).

Silica gel TLC: Rf=0.37 (CHCl$_3$).

EXAMPLE 10 a) 2-Hydroxyestradiol 17-acetate 3-methoxymethyl ether

To a solution of 2-hydroxyestradiol 2,17-diacetate 3-methoxymethyl ether (1.35 g, 3.24 mmol) obtained by the process described in Example 6-b in acetone (32.3 ml), a solution of KHCO$_3$ (647 mg, 6.46 mmol) in water (16.1 ml) and MeOH (80.7 ml) was added, and the mixture was stirred at room temperature for 22 hours and then 50° C. for 3 hours. After water (20 ml) was added to the reaction mixture, acetone and MeOH were removed by evaporation. The precipitate was collected by filtration, washed with water, and then dried in vacuo to afford 1.20 g (99.2%) of the titled compound.

$^1$H-NMR spectrum (CDCl$_3$) δ ppm: 0.82 (3H, s, 18-CH$_3$), 1.2–2.9 (15H, m, estrogen CH and CH$_2$), 2.05 (3H, S, C$_{17}$—OCOCH$_3$), 3.51 (3H, s, O—CH$_3$), 4.68 (1H, t like, C$_{17}$—H), 5.16 (2H, s, O—CH$_2$—O), 5.74 (1H, s, C$_2$—OH), 6.79 (1H, s, Ar C$_4$—H), and 6.89 (1H, s, Ar C$_1$—H).

Silica gel TLC: Rf=0.49 (hexane:AcOEt=2:1).

b) 2-Benzyloxyestradiol 17-acetate 3-methoxymethyl ether

To a solution of 2-hydroxyestradiol 17-acetate 3-methoxymethyl ether (1.13 g, 3.02 mmol) obtained by the process described in Example 10-a in EtOH (25 ml), k$_2$CO$_3$ (626 mg, 4.54 mmol) and benzyl chloride (0.452 ml, 3.93 mmol) were added and the mixture was refluxed for 4 hours. Additional amount of benzyl chloride (0.174 ml, 1.51 mmol) was added, and the mixture was refluxed for further 2 hours. After the reaction mixture was cooled to room temperature, it was then filtered to remove an insoluble material. The filtrate was evaporated in vacuo and a residue was mixed with water to obtain a precipitate. The precipitate was collected by filtration, washed with water, and then dried in vacuo to afford a mixture (1.44 g) of 2-benzyloxyestradiol 3-methoxymethyl ether and 2-benzyloxyestradiol 17-acetate 3-methoxymethyl ether.

A part (1.41 g) of the mixture of 2-benzyloxyestradiol 3-methoxymethyl ether and 2-benzyloxyestradiol 17-acetate 3-methoxymethyl ether obtained above was treated with pyridine (4.0 ml, 49.5 mmol) and acetic anhydride (3.0 ml, 31.7 mmol) for 23 hours at room temperature. The reaction mixture was poured onto ice (150 g), and 2N-HCl (40 ml) was added to it. After extraction with AcOEt, the organic layer was washed successively with 1N-HCl, saturated NaHCO$_3$ solution, water, and brine, thereafter it was dried over anhydrous Na$_2$SO$_4$ and evaporated in vacuo to obtain a crude product (1.51 g), which was, in turn, subjected to silica gel chromatography (elution solvent, hexane:AcOEt=6:1) to afford 1.35 g (98.5%) of the titled compound.

$^1$H-NMR spectrum (CDCl$_3$) δ ppm: 0.81 (3H, s, 18-CH$_3$), 1.1–2.9 (15H, m, estrogen CH and CH$_2$), 2.05 (3H, s, C$_{17}$—OCOCH$_3$), 3.51 (3H, s, O—CH$_3$), 4.68 (1H, t like, C$_{17}$—H), 5.10 (2H, s, C$_6$H$_5$CH$_2$), 5.18 (2H, s, O—CH$_2$—O), 6.85 (2H, s, Ar C$_4$—H and C$_1$—H), and 7.2–7.5 (5H, m, C$_6$H$_5$).

Silica gel TLC: Rf=0.50 (hexane:AcOEt=4:1).

c) 2-Benzyloxyestradiol 17-acetate

A mixture of 2-benzyloxyestradiol 17-acetate 3-methoxymethyl ether (3.70 g, 7.97 mmol) obtained by the process described in Example 10-b, acetic acid (20 ml), and 2N-HCl (2.0 ml) was stirred at room temperature for 1.5 hours. The reaction mixture was poured into water (500 ml), and the precipitate was collected by filtration, washed with water, and then dried in vacuo to obtain a crude product (3.41 g), which was, in turn, subjected to silica gel chromatography (elution solvent, hexane:AcOEt=6:1) to afford 3.02 g (90.1%) of the titled compound.

$^1$H-NMR spectrum (CDCl$_3$) δ ppm: 0.83 (3H, s, 18-CH$_3$), 1.1–2.9 (15H, m, estrogen CH and CH$_2$), 2.05 (3H, s, C$_{17}$—OCOCH$_3$), 4.69 (1H, t like, C$_{17}$—H), 5.06 (2H, s, C$_6$H$_5$CH$_2$), 6.65 (1H, s, Ar C$_4$—H), 6.85 (1H, s, Ar C$_1$—H), and 7.39 (5H, s, C$_6$H$_5$).

Silica gel TLC: Rf=0.37 (hexane:AcOEt=5:1).

EXAMPLE 11 a) 2-Hydroxyestradiol 3-methoxymethyl ether

A mixture of 2-hydroxyestradiol 2,17-diacetate 3-methoxymethyl ether (5.30 g, 12.7 mmol) obtained by the process described in Example 6-b, MeOH (106 ml), and 1N—NaOH (53 ml) was stirred at room temperature for 2.5 hours. After MeOH was removed by evaporation, acetic acid (2.37 ml) was added to the residue. After extraction with AcOEt, the organic layer was washed successively with saturated NaHCO$_3$ solution, water, and brine, thereafter it was dried over anhydrous Na$_2$SO$_4$ and evaporated in vacuo to afford 4.23 g (100%) of the titled compound.

$^1$H-NMR spectrum (CDCl$_3$) δ ppm: 0.77 (3H, s, 18-CH$_3$), 1.1–2.9 (15H, m, estrogen CH and CH$_2$), 3.51 (3H, s, O—CH$_3$), 3.73 (1H, t like, C$_{17}$—H), 5.16 (2H, s, O—CH$_2$—O), 5.75 (1H, br.s, C$_2$—OH), 6.79 (1H, s, Ar C$_4$—H), and 6.89 (1H, s, Ar C$_1$—H).

Silica gel TLC: Rf=0.20 (hexane:AcOEt=2:1).

b) 2-Benzyloxyestradiol 3-methoxymethyl ether

To a solution of 2-hydroxyestradiol 3-methoxymethyl ether (4.20 g, 12.6 mmol) obtained by the process described in Example 11-a in EtOH (100 ml), K$_2$CO$_3$ (2.62 g, 19.0 mmol) and benzyl chloride (1.89 ml, 16.4 mmol) were added, and the mixture was refluxed for 4 hours, Additional amount of benzyl chloride (0.73 ml, 6.33 mmol) was added, and the mixture was refluxed for further 2 hours. After the reaction mixture was cooled to room temperature, it was then filtered to remove an insoluble material. The filtrate was concentrated in vacuo and a residue was mixed with water to obtain a precipitate. The precipitate was collected by filtration, washed with water, and then dried in vacuo to obtain a crude product (5.64 g).

A part (1.50 g) of the crude product was subjected to silica gel chromatography (elution solvent, hexane:AcOEt=3:1) to afford 1.40 g (98.6%) of the titled compound.

$^1$H-NMR spectrum (CDCl$_3$) δ ppm: 0.76 (3H, s, 18-CH$_3$), 1.0–2.9 (15H, m, estrogen CH and CH$_2$), 3.51 (3H, s, O—CH$_3$), 3.72 (1H, t like, C$_{17}$—H), 5.10 (2H, s, C$_6$H$_5$CH$_2$), 5.19 (2H, s, O—CH$_2$—O), 6.85 (1H, s, Ar C$_4$—H), 6.88 (1H, s, Ar C$_1$—H), and 7.2–7.5 (5H, m, C$_6$H$_5$).

Silica gel TLC: Rf=0.38 (hexane:AcOEt=2:1).

c) 2-Benzyloxyestradiol 17-acetate 3-methoxymethyl ether

A mixture of another part (4.00 g) of the crude product of 2-benzyloxyestradiol 3-methoxymethyl ether obtained by the process described in Example 11-b, pyridine (12 ml, 148 mmol), and acetic anhydride (9.0 ml, 95.2 mmol) was stirred for 23 hours at room temperature. The reaction mixture was poured onto ice (200 g) and 2N-HCl (200 ml) was added to it. After extraction with AcOEt, the organic layer was washed successively with 1N-HCl, saturated NaHCO$_3$ solution, water, and brine, thereafter it was dried over anhydrous Na$_2$SO$_4$ and evaporated in vacuo to obtain a crude product (4.36 g), which was, in turn, subjected to silica gel chromatography (elution solvent, hexane:AcOEt=6:1) to afford 3.93 g (94.7% from 2-hydroxyestradiol 3-methoxymethyl ether) of the titled compound.

This compound showed the same physico-chemical data to those described in Example 10-b.

This compound can be converted into 2-benzyloxyestradiol 17-acetate by the process described in Example 10-c.

EXAMPLE 12 a) 2-Benzyloxyestradiol

A mixture of the purified 2-benzyloxyestradiol 3-methoxymethyl ether (1.35 g, 3.19 mmol) obtained by the process described in Example 11-b, MeOH (27 ml), and concentrated HCl (2.7 ml) was stirred for 2 hours at room temperature. After removal of a half volume of MeOH by evaporation, the residue was poured into water (300 ml). The precipitate was collected by filtration, washed with water, and then dried in vacuo to afford 1.20 g (99.2%) of the titled compound.

$^1$H-NMR spectrum (CDCl$_3$) δ ppm: 0.78 (3H, s, 18-CH$_3$), 1.0–2.9 (15H, m, estrogen CH and CH$_2$), 3.73 (1H, t like, C$_{17}$—H), 5.07 (2H, s, C$_6$H$_5$CH$_2$), 6.66 (1H, s, Ar C$_4$—H), 6.87 (1H, s, Ar C$_1$—H), and 7.40 (5H, s, C$_6$H$_5$).

Silica gel TLC: Rf=0.37 (hexane:AcOEt=2:1).

b) 2-Benzyloxyestradiol diacetate

A mixture of 2-benzyloxyestradiol (1.18 g, 3.12 mmol) obtained by the process described in Example 12-a, pyridine (3.0 ml, 37.1 mmol), and acetic anhydride (2.5 ml, 26.4 mmol) was stirred for 21 hours at room temperature. The reaction mixture was poured onto ice and the precipitate was collected by filtration, washed with water, and then dried in vacuo to afford 1.40 g (97.2%) of the titled compound.

$^1$H-NMR spectrum (CDCl$_3$) δ ppm: 0.82 (3H, s, 18-CH$_3$), 1.1–2.9 (15H, m, estrogen CH and CH$_2$), 2.06 (3H, s, C$_{17}$—OCOCH$_3$), 2.26 (3H, s, C$_3$—OCOCH$_3$), 4.68 (1H, t like, C$_{17}$—H), 5.04 (2H, s, C$_6$H$_5$CH$_2$), 6.75 (1H, s, Ar C$_4$—H), 6.93 (1H, s, Ar C$_1$—H), and 7.36 (5H, s, C$_6$H$_5$).

Silica gel TLC: Rf=0.42 (hexane:AcOEt=4:1).

c) 2-Benzyloxyestradiol 17-acetate

To a solution of 2-benzyloxyestradiol diacetate (1.35 g, 2.92 mmol) obtained by the process described in Example 12-b in acetone (29.2 ml), a solution of KHCO$_3$ (585 mg) in water (14.6 ml) and MeOH (73.0 ml) was added, and the mixture was stirred at room temperature for 21 hours, followed at 50° C. for 6 hours. After water was added to the reaction mixture, acetone and MeOH were removed by evaporation. The precipitate was collected by filtration, washed with water, and then dried in vacuo to obtain a crude product (1.23 g), which was, in turn, subjected to silica gel chromatography (elution solvent, hexane:AcOEt=6:1) to afford 1.18 g (95.9%) of the titled compound.

This compound showed the same physico-chemical data to those described in Example 10-c.

EXAMPLE 13 a) 2,3,4,6-Tetra-O-acetyl-1-O-(17β-acetoxy-2-benzyloxy-1,3,5(10)-estratriene-3-yl)-β-D-glucopyranoside CdCO$_3$ (6.55 g, 38.0 mol) was added to a solution of 2-benzyloxyestradiol 17-acetate (4.00 g, 9.49 mmol) obtained by the process described in Example 10-c in toluene (250 ml), and the suspension was distilled until 50 ml of toluene had been removed. A solution of acetobromoglucose (11.7 g, 28.5 mmol) in toluene (300 ml) was added dropwise to the stirred mixture over 6 hours and an equal volume of toluene was simultaneously distilled to give a constant volume of the reaction mixture. Distillation was continued for further 15 hours during which generated moisture was removed. Additional amounts of CdCO$_3$ (6.55 g) and acetobromoglucose (11.7 g) were added, and the mixture was refluxed for further 18 hours during which generated moisture was removed. An insoluble material was removed off by filtration through a pad of Celite. The filtrate was evaporated in vacuo to obtain a crude product, which was, in turn, subjected to silica gel chromatography (elution solvent, hexane:AcOEt=2:1) to afford 4.30 g (60.3%) of the titled compound.

$^1$H-NMR spectrum (CDCl$_3$) δ ppm: 0.82 (3H, s, 18-CH$_3$), 1.1–2.9 (30H, m, estrogen CH and CH$_2$, and OCOCH$_3$ x 5), 3.78 (1H, m, pyranose C$_5$—H), 4.0–4.4 (2H, m, pyranose C$_6$—H$_2$), 4.69 (1H, t like, C$_{17}$—H), 4.9–5.4 (6H, m, pyranose C$_1$—H, C$_2$—H, C$_3$—H, C$_4$—H, and C$_6$H$_5$CH$_2$), 6.83 (1H, s, Ar C$_4$—H or C$_1$—H), 6.88 (1H, s, Ar C$_1$—H or C$_1$—H), and 7.2–7.5 (5H, m, C$_6$H$_5$).

Silica gel TLC: Rf=0.26 (hexane:AcOEt=2:1).

b) 1-O-(2-Benzyloxy-17β-hydroxy-1,3,5(10)-estratriene-3-yl)-β-D-glucopyranoside

To 2,3,4,6-tetra-O-acetyl-1-O-(17β-acetoxy-2-benzyloxy-1,3,5(10)-estratriene-3-yl)-β-D-glucopyranoside (4.20 g, 5.59 mmol) obtained by the process described in Example 13-a, MeOH (80 ml) and 1N-NaOH (40 ml) were added. The mixture was stirred at room temperature for 1.5 hours and then at 45° C. for 1 hour. After removal of MeOH by evaporation, an aqueous layer was separated from an oily residue by decantation. The aqueous layer was extracted with AcOEt. The AcOEt layer and the oily residue were combined and concentrated in vacuo to obtain a crude product (2.71 g), which was, in turn, subjected to silica gel chromatography (elution solvent, CHCl$_3$:MeOH=8:1) to afford 2.25 g (74.5%) of the titled compound.

$^1$H-NMR spectrum (CD$_3$OD) δ ppm: 0.73 (3H, s, 18-CH$_3$), 1.0–2.8 (15H, m, estrogen CH and CH$_2$), 3.3–3.9 (7H, m, C$_{17}$—H, and pyranose C$_2$—H, C$_3$—H, C$_4$—H, C$_5$—H and C$_6$—H$_2$), 4.84–4.91 (1H, m, pyranose C$_1$—H), 5.06 (2H, s, C$_6$H$_5$CH$_2$), 6.88 (2H, s, Ar C$_4$—H and C$_1$—H), and 7.2–7.5 (5H, m, C$_6$H$_5$).

Silica gel TLC: Rf=0.55 (CHCl$_3$:MeOH=5:1).

c) 2-Hydroxyestradiol 3-(β-D-glucopyranoside)

To a solution of 1-O-(2-benzyloxy-17β-hydroxy-1,3,5(10)-estratriene-3-yl)-β-D-glucopyranoside (2.03 g, 3.75 mmol) obtained by the process described in Example 13-b in MeOH (100 ml), a suspension of 5% Pd/C (0.50 g) in MeOH (50 ml) was added, and the mixture was stirred under bubbling of H$_2$ for 2 hours. The catalyst Pd/C was removed off by filtration through a pad of Celite. The filtrate was evaporated in vacuo to obtain a crude product (1.65 g), which was, in turn, subjected to silica gel chromatography (elution solvent, CHCl$_3$:MeOH=5:1) to afford 1.57 g (92.9%) of the titled compound.

$^1$H-NMR spectrum (CD$_3$OD) δ ppm: 0.74 (3H, s, 18-CH$_3$), 1.0–2.8 (15H, m, estrogen CH and CH$_2$), 3.3–4.0 (7H, m, C$_{17}$—H, and pyranose C$_2$—H, C$_3$—H, C$_4$—H, C$_5$—H and C$_6$—H$_2$), 4.65–4.73 (1H, m, pyranose C$_1$—H), 6.77 (1H, s, Ar C$_4$—H), and 6.85 (1H, s, Ar C$_1$—H).

$^{13}$C-NMR spectrum (DMSO-d$_6$) δ ppm: 11.11, 22.71, 25.95, 26.98, 28.50, 29.85, 36.57, 38.41, 42.69, 43.62, 49.52, 60.79, 69.84, 73.30, 75.85, 77.10, 79.97, 103.00, 112.59, 117.62, 126.73, 134.75, 143.04, and 144.66.

IR spectrum (KBr) cm$^{-1}$: 3408, 2920, 2868, 1588, 1502, 1436, 1408, 1384, 1352, 1282, 1210, 1068, 1040, 886, 864, 830, and 810.

Silica gel TLC: Rf=0.24 (CHCl$_3$:MeOH=5:1).
Solubility: 1.0 mg/3 ml (H$_2$O).

EXAMPLE 14 a) 2,3,4,6-Tetra-O-acetyl-1-O-(2-acetyl-17β-acetoxy-1,3,5(10)-estratriene-3-yl)-β-D-glucopyranoside and 2,3,4,6-tetra-O-acetyl-1-O-(2-acetyl-17β-acetoxy-1,3,5(10)-estratriene-3-yl)-α-D-glucopyranoside CdCO$_3$ (1.72 g, 10.0 mmol) was added to a solution of 2-acetylestradiol 17-acetate (891 mg, 2.50 mmol) obtained by the process described in Example 1-b in toluene (50 ml), and the suspension was distilled until 15 ml of toluene had been removed. A solution of acetobromoglucose (3.08 g, 7.50 mmol) in toluene (50 ml) was added dropwise to the stirred mixture over 2 hours and an equal volume of toluene was simultaneously distilled to give a constant volume of the reaction mixture. Distillation was continued for further 2 hours during which toluene was added dropwise to maintain the volume of the suspension. Since preliminary TLC analysis showed that the starting material had not been completely consumed, CdCO$_3$ (0.86 g, 5.00 mmol) was added to the suspension and subsequently a solution of acetobromoglucose (1.54 g, 3.75 mmol) in toluene (30 ml) was further added dropwise over 1 hour, and an equal volume of toluene was simultaneously distilled to give a constant volume of the reaction mixture. Distillation was continued for further 1.5 hours during which toluene was added dropwise to maintain the volume of the suspension.

An insoluble material was removed off by filtration through a pad of Celite. The filtrate was evaporated in vacuo to obtain a crude product, which was, in turn, subjected to silica gel chromatography (elution solvent, hexane:AcOEt=2:1) to afford 662 mg (38.5%) of 2,3,4,6-tetra-O-acetyl-1-O-(2-acetyl-17β-acetoxy-1,3,5(10)-estratriene-3-yl)-β-D-glucopyranoside and 1.23 g (purity 67%, net weight 824 mg, yield 47.9%) of 2,3,4,6-tetra-O-acetyl-1-O-(2-acetyl-17β-acetoxy-1,3,5(10)-estratriene-3-yl-α-D-glucopyranoside.

Physico-chemical data;

2,3,4,6-tetra-O-acetyl-1-O-(2-acetyl-17β-acetoxy-1,3,5(10)-estratriene-3-yl)-β-D-glucopyranoside $^1$H-NMR spectrum (CDCl$_3$) δ ppm: 0.82 (3H, s, 18-CH$_3$), 1.2–3.0 (30H, m, estrogen CH and CH$_2$, and OCOCH$_3$ x 5), 2.52 (3H, s, C$_2$—COCH$_3$), 3.8–4.3 (3H, m, pyranose C$_5$—H and C$_6$—H$_2$), 4.68 (1H, t like, C$_{17}$—H), 5.1–5.4 (4H, m, pyranose C$_1$—H, C$_2$—H, C$_3$—H and C$_4$—H), 6.76 (1H, s, Ar C$_4$—H), and 7.61 (1H, s, Ar C$_1$—H).

Silica gel TLC: Rf=0.12 (hexane:AcOEt=2:1).

2,3,4,6-tetra-O-acetyl-1-O-(2-acetyl-17β-acetoxy-1,3,5(10)-estratriene-3-yl)-α-D-glucopyranoside $^1$H-NMR spectrum (CDCl$_3$) δ ppm: 0.83 (s, 18-CH$_3$), 1.2–3.0 (m, estrogen CH and CH$_2$, and OCOCH$_3$ x 5), 2.73 (s, C$_2$—COCH$_3$), 3.8–4.4 (m, pyranose C$_5$—H and C$_6$—H$_2$), 4.68 (t like, C$_{17}$—H), 5.0–5.8 (m, pyranose C$_1$—H, C$_2$—H, C$_3$—H and C$_4$—H), 6.96 (s, Ar C$_4$—H), and 7.68 (s, Ar C$_1$—H).

Silica gel TLC: Rf=0.18 (hexane:AcOEt=2:1).

b) 2,3,4,6-Tetra-O-acetyl-1-O-(2,17β-diacetoxy-1,3,5(10)-estratriene-3-yl)-β-D-glucopyranoside A mixture of 2,3,4,6-tetra-O-acetyl-1-O-(2-acetyl-17β-acetoxy-1,3,5(10)-estratriene-3-yl)-β-D-glucopyranoside (395 mg, 0.575 mmol) obtained by the process described in Example 14-a, m-chloroperbenzoic acid (298 mg, 1.73 mmol), Na$_2$HPO$_4$ (245 mg, 1.73 mmol), and CHCl$_3$ (8 ml) was stirred at room temperature for 17 hours. After an insoluble material was removed off by filtration, the filtrate was poured into ice-cooled ether. The organic layer was washed successively with 5% Na$_2$CO$_3$ solution, water, and brine, thereafter it was dried over anhydrous Na$_2$SO$_4$ and evaporated in vacuo to afford 440 mg of the titled compound as a crude product.

$^1$H-NMR spectrum (CDCl$_3$) δ ppm: 0.80 (3H, s, 18-CH$_3$), 1.1–3.0 (30H, m, estrogen CH and CH$_2$, and OCOCH$_3$ x 5), 2.25 (3H, s, C$_2$—OCOCH$_3$), 3.8–4.4 (3H, m, pyranose C$_5$—H and C$_6$—H$_2$), 4.68 (1H, t like, C$_{17}$—H), 5.0–5.4 (4H, m, pyranose C$_1$—H, C$_2$—H, C$_3$—H and C$_4$—H), 6.71 (1H, s, Ar C$_4$—H), and 6.93 (1H, s, Ar C$_1$—H).

Silica gel TLC: Rf=0.56 (CHCl$_3$:MeOH=20:1).

c) 2-Hydroxyestradiol 3-(β-D-glucopyranoside)

To the crude product of 2,3,4,6-tetra-O-acetyl-1-O-(2,17β-diacetoxy-1,3,5(10)-estratriene-3-yl)-β-D-glucopyranoside (400 mg) obtained by the process described in Example 14-b, MeOH (10 ml) and 1N-NaOH (5 ml) were added. The mixture was stirred at room temperature for 1.5 hours. After removal of MeOH by evaporation, water (15 ml) and acetic acid (0.150 ml) were added to precipitate the desired product. The precipitate was collected by filtration and subjected to silica gel chromatography (elution solvent, CHCl$_3$:MeOH=5:1) to afford 196 mg [83.1% from 2,3,4,6-tetra-O-acetyl-1-O-(2-acetyl-17β-acetoxy-1,3,5(10)-estratriene-3-yl)-β-D-glucopyranoside] of the titled compound.

Physico-chemical data of this compound were the same to those described in Example 13-c.

EXAMPLE 15 a) 2,3,4,6-Tetra-O-acetyl-1-O-(2,17β-diacetoxy-1,3,5(10)-estratriene-3-yl)-α-D-glucopyranoside A mixture of 2,3,4,6-tetra-O-acetyl-1-O-(2-acetyl-17β-acetoxy-1,3,5(10)-estratriene-3-yl)-α-D-glucopyranoside (790 ml) purity 67%, net weight 529 mg, 0.771 mmol) obtained by the process described in Example 14-a, m-chloroperbenzoic acid (596 mg, 3.45 mmol), Na$_2$HPO$_4$ (490 mg, 3.45 mmol), and CHCl$_3$ (16 ml) was stirred at room temperature for 22 hours. After an insoluble material was removed off by filtration, the filtrate was poured into ice-cooled ether. The organic layer was washed successively with 5% Na$_2$CO$_3$ solution, water, and brine, thereafter it was dried over anhydrous Na$_2$SO$_4$ and evaporated in vacuo to afford 863 mg of the titled compound as a crude product.

$^1$H-NMR spectrum (CDCl$_3$) δ ppm: 0.82 (s, 18-CH$_3$), 1.1–2.9 (m, estrogen CH and CH$_2$, and OCOCH$_3$ x 5), 2.37 (s, C$_2$—OCOCH$_3$), 3.7–4.4 (m, pyranose C$_5$—H and C$_6$—H$_2$), 4.69 (t like, C$_{17}$—H), 4.9–5.8 (m, pyranose C$_1$—H, C$_2$—H, C$_3$—H and C$_4$—H), 6.91 (s, Ar C$_4$—H), and 6.98 (s, Ar C$_1$—H).

Silica gel TLC: Rf=0.44 (CHCl$_3$:MeOH=50:1).

b) 2-Hydroxyestradiol 3-(α-D-glucopyranoside)

To the crude product of 2,3,4,6-tetra-O-acetyl-1-O-(2,17β-diacetoxy-1,3,5(10)-estratriene-3-yl)-α-D-glucopyranoside (850 mg) obtained by the process described in Example 15-a, MeOH (20 ml) and 1N-NaOH (10 ml) were added. The mixture was stirred at room temperature for 1 hour. After removal of MeOH by evaporation, water (50 ml) and acetic acid (0.366 ml) were added to precipitate the desired product. The muddy precipitate was collected by filtration and crystallized from MeOH to afford 240 mg [70.4% from 2,3,4,6-tetra-O-acetyl-1-O-(2-acetyl-17β-acetoxy-1,3,5(10)-estratriene-3-yl)-α-D-glucopyranoside] of the titled compound.

$^1$H-NMR spectrum (DMSO-d$_6$:CD$_3$OD=3:1) δ ppm: 0.71 (3H, s, 18-CH$_3$a), 1.0–2.8 (15H, m, estrogen CH and CH$_2$), 3.3–3.9 (7H, m, C$_{17}$—H, and pyranose C$_2$—H, C$_3$—H, C$_4$—H, C$_5$—H and C$_6$—H$_2$), 5.14 (1H, d, J=3 Hz, pyranose C$_1$—H), 6.73 (1H, s, Ar C$_4$—H), and 6.88 (1H, s, Ar C$_1$—H).

$^{13}$C-NMR spectrum (DMSO-d$_6$) β ppm: 11.16, 22.70, 26.01, 27.04, 28.39, 29.91, 36.68, 38.36, 42.75, 43.67, 49.58, 60.68, 69.95, 71.95, 73.14, 73.58, 80.02, 100.50, 112.53, 118.01, 126.68, 134.80, 143.04, and 145.14.

Silica gel TLC: Rf=0.23 (CHCl$_3$:MeOH=5:1).

EXAMPLE 16 a) 2-Hydroxyestradiol 17-acetate 3-benzyl ether

To a solution of 2-hydroxyestradiol 2,17-diacetate 3-benzyl ether (9.00 g, 19.4 mmol) obtained by the process described in Example 7-b in acetone (450 ml), a solution of KHCO$_3$ (9.00 g) in water (225 ml) and MeOH (1125 ml) was added, and the mixture was stirred at room temperature for 47 hours. The mixture was poured into ether (6000 ml), and the organic layer was washed successively with water, and brine, thereafter it was dried over anhydrous Na$_2$SO$_4$ and evaporated in vacuo to obtain a crude product (8.15 g), which was, in turn, subjected to silica gel chromatography (elution solvent, CHCl$_3$) to afford 7.59 g (92.8%) of the titled compound.

$^1$H-NMR spectrum (CDCl$_3$) δ ppm: 0.82 (3H, s, 18-CH$_3$), 1.1–2.9 (15H, m, CH and CH$_2$), 2.05 (3H, s, C$_{17}$—OCOCH$_3$), 4.68 (1H, t like, C$_{17}$—H), 5.05 (2H, s, C$_6$H$_5$CH$_2$), 5.50 (1H, s, ·OH), 6.64 (1H, s, C$_4$—H), 6.89 (1H, s, $\overline{C_1}$—H), and 7.39 (5H, br.s, C$_6$H$_5$).

Silica gel TLC: Rf=0.36 (CHCl$_3$).

b) 2,3,4,6-Tetra-O-acetyl-1-O-(17β-acetoxy-3-benzyloxy-1,3,5(10)-estratriene-2-yl)-β-D-glucopyranoside CdCO$_3$ (6.55 g, 38.0 mmol) was added to a solution of 2-hydroxyestradiol 17-acetate 3-benzyl ether (4.00 g, 9.51 mmol) obtained by the process described in Example 16-a in benzene (300 ml), and the suspension was distilled until 100 ml of benzene had been removed. A solution of acetobromoglucose (11.7 g, 28.5 mmol) in benzene (300 ml) was added dropwise to the stirred mixture over 3 hours and an equal volume of benzene was simultaneously distilled to give a constant volume of the reaction mixture. Heating was continued further. After 30 minutes, additional amount of CdCO$_3$ (6.60 g, 38.3 mmol) was added, and after 19 hours, additional amounts of CdCO$_3$ (5.0 g, 29.0 mmol) and acetobromoglucose (5.3 g, 12.9 mmol) in benzene (100 ml) were further added. The mixture was refluxed for further 23 hours, meanwhile generated moisture was removed. An insoluble material was removed off by filtration through a pad of Celite and washed with benzene. The filtrate and washings were combined and evaporated in vacuo to obtain a crude product, which was, in turn, subjected to silica gel chromatography (elution solvent, hexane:AcOEt=2:1) to afford 4.51 g (63.3%) of the titled compound.

$^1$H-NMR spectrum (CDCl$_3$) δ ppm: 0.82 (3H, s, 18-CH$_3$), 1.1–2.9 (30H, m, estrogen CH and CH$_2$, and OCOCH$_3$ x 5), 3.73 (1H, m, pyranose C$_5$—H), 4.0–4.4 (2H, m, pyranose C$_6$—H$_2$), 4.68 (1H, t like, C$_{17}$—H), 4.9–5.4 (6H, m, pyranose C$_1$—H, C$_2$—H, C$_3$—H, C$_4$—H, and C$_6$H$_5$CH$_2$), 6.67 (1H, s, Ar C$_4$—H), 7.07 (1H, s, Ar C$_1$—H), and 7.2–7.5 (5H, m, C$_6$H$_5$H).

$^{13}$C-NMR spectrum (DMSO-d$_6$) δ ppm: 11.81, 19.99, 20.16, 20.26, 20.75, 22.70, 25.57, 26.77, 27.14, 28.61, 36.46, 37.93, 42.42, 43.34, 49.03, 61.98, 68.27, 70.11, 70.81, 72.00, 81.81, 98.77, 115.08, 115.62, 127.22, 127.49, 128.14, 131.55, 132.42, 137.24, 144.01, 146.51, 168.83, 169.20, 169.42, 169.80, and 170.18.

IR spectrum (KBr) cm$^{-1}$: 2936, 2872, 1756, 1508, 1434, 1372, 1246, 1222, 1042, and 906.

MS spectrum (EI/DI) m/z: 750 (M+).

Silica gel TLC: Rf=0.27 (hexane:AcOEt=2:1).

c) 1-O-(3-Benzyloxy-17β-hydroxy-1,3,5(10)-estratriene-2-yl)-β-D-glucopyranoside

To 2,3,4,6-tetra-O-acetyl-1-O-(17β-acetoxy-3-benzyloxy-1,3,5(10)-estratriene-2-yl)-β-D-glucopyranoside (3.80 g, 5.06 mmol) obtained by the process described in Example 16-b, MeOH (266 ml) was added. After the mixture was mildly heated to obtain a homogeneous solution, 1N-NaOH (76 ml) was added, and the mixture was stirred at room temperature for 1.5 hours. After removal of MeOH by evaporation, the residue was extracted with AcOEt. The organic layer was washed with brine, dried over anhydrous $Na_2SO_4$, and concentrated in vacuo to obtain a crude product (2.68 g), which was, in turn, subjected to silica gel chromatography (elution solvent, $CHCl_3$:MeOH=7:1) to afford 2.36 g (86.1%) of the titled compound.

$^1$H-NMR spectrum ($CD_3OD$) δ ppm: 0.77 (3H, s, 18-$CH_3$). 1.0–2.8 (15H, m, estrogen CH and $CH_2$). 3.2–4.0 (7H, m, $C_{17}$—H, and pyranose $C_2$—H, $C_3$—H, $C_4$—H, $C_5$—H and $C_6$—H). 4.82–4.90 (1H, m, pyranose $C_1$—H), 5.09 (2H, s, $C_6H_5CH_2$). 6.71 (1H, s, Ar $C_4$—H), 7.13 (1H, s, Ar $C_1$—H), and 7.2–7.6 (5H, m, $C_6H_5$).

$^{13}$C-NMR spectrum (DMSO-$d_6$) δ ppm: 11.16, 22.70, 25.68, 26.87, 28.50, 29.85, 36.68, 38.36, 42.75, 43.67, 49.52, 60.74, 69.79, 70.60, 73.36, 76.83, 76.94, 79.97, 101.37, 114.48, 115.78, 127.38, 128.08, 129.87, 133.07, 137.62, 145.26, and 146.01.

IR spectrum (KBr) cm$^{-1}$: 3400, 2920, 2868, 1504, 1454, 1412, 1382, 1324, 1286, 1260, 1210, 1072, 888, 748, and 698.

Silica gel TLC: Rf=0.44 ($CHCl_3$:MeOH=5:1).

d) 2-Hydroxyestradiol 2-(β-D-glucopyranoside)

To a solution of 1-O-(3-benzyloxy-17β-hydroxy-1,3,5(10)-estratriene-2-yl)-β-D-glucopyranoside (2.30 g, 4.25 mmol) obtained by the process described in Example 16-c in MeOH (250 ml), a suspension of 5% Pd/C (1.00 g) in MeOH (100 ml) was added, and the mixture was stirred under bubbling of $H_2$ for 2 hours. The catalyst Pd/C was removed off by filtration through a pad of Celite. The filtrate was evaporated in vacuo to obtain a crude product (1.85 g), which was, in turn, subjected to silica gel chromatography (elution solvent, $CHCl_3$:MeOH=5:1) to afford 1.74 g (91.1%) of the titled compound.

$^1$H-NMR spectrum ($CD_3OD$) β ppm: 0.74 (3H, s, 18-$CH_3$), 0.9–2.9 (15H, m, estrogen CH and $CH_2$), 3.3–4.0 (7H, m, $C_{17}$—H, and pyranose $C_2$—H, $C_3$—H, $C_4$H, $C_5$—H and $C_{62}$), 4.6–4.8 (1H, m, pyranose $C_1$—H), 6.52 (1H, s, Ar $C_4$—H), and 7.11 (1H, s, Ar $C_1$—H).

$^{13}$C-NMR spectrum (DMSO-$d_6$) δ ppm: 11.16, 22.76, 25.84, 26.93, 28.44, 29.91, 36.63, 38.52, 42.75, 43.67, 49.52, 60.85, 69.89, 73.36, 75.96, 77.10, 80.02, 103.38, 114.86, 115.57, 130.90, 143.31, and 144.71.

IR spectrum (KBr) cm$^{-1}$: 3368, 2920, 2864, 1502, 1434, 1380, 1354, 1322, 1292, 1264, 1204, 1068, and 884.

Silica gel TLC: Rf=0.21 ($CHCl_3$:MeOH=5:1).

Solubility: 1.5 mg/0.5–1 ml ($H_2O$).

Test Example 1

(Inhibitory effect of 2-hydroxyestradiol 17-glucoside on the lipid peroxidation of low-density lipoprotein)

Low-density lipoprotein (LDL) was prepared from hypercholesterolemic rabbit serum. 2-Hydroxyestradiol 17-(β-D-glucopyranoside) (2-$OHE_2$ 17-Glu) obtained according to the method of this invention (Example 4) was dissolved in distilled water and 2-hydroxyestradiol (2-$OHE_2$) as a reference compound, in dimethylsulfoxide (DMSO), to give a final concentration of 500 μM. The reaction mixture contained the followings in a final volume of 1 ml: 500 μg of LDL; 5 nmol of $CuSO_4$; and 5 nmol of either 2-$OHE_2$ 17-Glu or 2-$OHE_2$. As blank tests, distilled water or DMSO was added in place of 2-$OHE_2$ 17-Glu or 2-$OHE_2$. After incubation for a definite time at 30° C., the amount of lipid hydroperoxides generated was determined by the methylene blue method. Results are shown in following Table 1. It was found that 2-$OHE_2$ 17-Glu clearly inhibited the peroxidation of LDL and that its inhibitory potency was the same to that of 2-$OHE_2$.

TABLE 1

| Compounds | Incubation time | | | |
|---|---|---|---|---|
| | 1 hr. | 2 hr. | 3 hr. | 4 hr. |
| 2-$OHE_2$ 17-Glu | 8.93 | 19.48 | 24.76 | 32.17 |
| Water | 35.41 | 80.36 | 123.79 | 167.72 |
| 2-$OHE_2$ | 17.45 | 24.55 | 27.29 | 30.74 |
| DMSO | 35.51 | 74.35 | 115.77 | 150.07 |

Values in Table 1 indicate the amount of lipid peroxides (nmol/mg protein).

Test Example 2

(Inhibitory effect of 2-hydroxyestradiol 2-glucoside on the lipid peroxidation of rat brain homogenate)

2-Hydroxyestradiol 2-(β-D-glucopyranoside) (2-$OHE_2$ 2-Glu) obtained according to the method of this invention (Example 16) was dissolved in water to give a concentration of 1 nM or 0.5 mM. The reaction mixture contains the followings in a final volume of 2 ml: 1.98 ml of rat brain homogenate (10 mg protein/ml) and 2-$OHE_2$ 2-Glu at a concentration of 5 μM or 10 μM. After incubation at 37° C., lipid peroxide level was determined by the thiobarbituric acid method.

Following Table 2 clearly shows that 2-$OHE_2$ 2-Glu strongly inhibited the lipid peroxidation in a concentration dependent manner.

TABLE 2

| Compounds | Incubation time | | | |
|---|---|---|---|---|
| | 0 hr. | 1 hr. | 2 hr. | 4 hr. |
| 2-$OHE_2$ 2-Glu (10 μM) | 0.271 | 0.905 | 1.326 | 1.534 |
| 2-$OHE_2$ 2-Glu (5 μM) | 0.271 | 1.124 | 1.867 | 3.167 |
| Water | 0.258 | 1.532 | 2.761 | 4.659 |

Values in Table 2 indicate the amount of lipid peroxides (nmol/mg protein) in terms of malondialdehyde.

Test Example 3

(Inhibitory effect of 2-hydroxyestradiol 2-glucoside on the lipid peroxidation of rat liver homogenate)

A rat liver homogenate was prepared in 4 volume of 0.15M KCl. 2-$OHE_2$ 2-Glu was dissolved in distilled water and 2-$OHE_2$, in 1% DMSO, to give a final concentration of 1 nM. The reaction mixture contained the followings in a final volume of 2 ml; 1.98 ml of rat liver homogenate (10 mg protein/ml) and 10 μM either 2-$OHE_2$ 2-Glu or 2-$OHE_2$. As blank tests, the same volume of distilled water or 1% DMSO was added in place of 2-$OHE_2$ 2-Glu or 2-$OHE_2$. After incubation for 4 hours at 37° C., lipid peroxide level was determined by the thiobarbituric acid method. It was found that 2-

OHE$_2$ 2-Glu and 2-OHE$_2$ inhibited the lipid peroxidation by 77% and 73%, respectively.

Test Example 4

(Incorporation of glycosides of 2-hydroxyestradiol into red blood cells)

The reaction mixture contained 0.2 nmol of 2-OHE$_2$, 2-OHE$_2$ 17-Glu, or 2-hydroxyestradiol 17-($\beta$-maltoside) (2-OHE$_2$ 17-Mal, obtained in Example 5) in 0.1 ml of 0.2% DMSO-0.1% ascorbic acid in phosphate buffered saline (PBS) and 0.9 ml of suspension of red blood cells in PBS. After incubation at 37° C. for several intervals, the mixture was centrifuged and supernatant fraction was obtained, and then the amount of each glycoside of 2-hydroxyestradiol remained in the supernatant was determined by HPLC. Following Table 3 shows that the incorporation of 2-OHE$_2$ 17-Glu and 2-OHE$_2$ 17-Mal into red blood cells was markedly retarded as compared with that of 2-OHE$_2$. This fact indicates that glycosylated compounds of 2-OHE$_2$ are advantageous in a point of view as a long-acting drug.

TABLE 3

| Incubation time | 2-OHE$_2$ | 2-OHE$_2$ 17-Glu | 2-OHE$_2$ 17-Mal |
|---|---|---|---|
| 0.5 min. | 4.4 | 74.7 | 102 |
| 1.0 min. | 4.4 | 54.1 | 90.1 |
| 2.0 min. | 3.7 | 39.9 | 80.3 |
| 3.0 min. | — | 20.6 | 86.9 |
| 4.0 min. | — | 16.7 | 77.1 |
| 5.0 min. | — | 13.5 | 81.0 |

Values in Table 3 indicate residual amount (%) in the incubation medium.
-: not determined.

Test Example 5

(Acute toxicity)

Male mice of ddY strain were received 2-OHE$_2$ 17-Glu or 2-OHE$_2$ 2-Glu by an intraperitoneal injection at doses of 250 mg, 500 mg, 750 mg, or 1000 mg/kg body weight. All mice survived over an observation period of 2 weeks and no abnormal symptom was found. Therefore, LD$_{50}$ of the glycosides was found to be over 1000 mg/kg body weight.

Medicine Preparation Example 1

(Drip infusion)

Ingredients listed below were blended in a conventional manner to prepare a drip infusion.

| Prescription: | |
|---|---|
| Glycoside of catechol estrogen | 50 mg |
| Ascorbic acid | 5 mg |
| Isotonic sodium chloride solution | 250 ml |

Medicine Preparation Example 2

(Subcutaneous injection)

Ingredients listed below were blended in a conventional manner to prepare a subcutaneous injection.

| Prescription: | |
|---|---|
| Glycoside of catechol estrogen | 10 mg |
| Propylene glycol | 0.8 ml |
| Distilled water for injection | 1.2 ml |

Medicine Preparation Example 3

(Tablet)

With use of following ingredients, a tablet was prepared in a conventional manner.

| Prescription: | |
|---|---|
| Glycoside of catechol estrogen | 50 (mg) |
| Lactose | 50 |
| Starch | 145 |
| Talc | 4 |
| Magnesium stearate | 1 |

What is claimed is:

1. A glycoside of catechol estrogen having the formula of

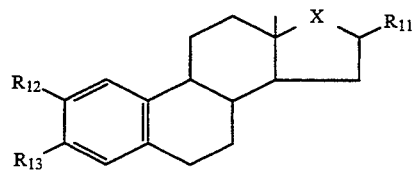

wherein X is carbonyl group or

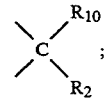

R$_{10}$ is hydroxyl group or glycosyloxy group, and R$_2$ is a hydrogen atom or ethynyl group; R$_{11}$ is a hydrogen atom, hydroxyl group, or glycosyloxy group; R$_{12}$ is hydroxyl group or glycosyloxy group; and R$_{13}$ is hydroxyl group or glycosyloxy group,
in which glycosyloxy group is selected from the group consisting of glucosyloxy, galactosyloxy, mannosyloxy, arabinosyloxy, ribosyloxy, xylosyloxy, fructosyloxy, rhamnosyloxy, fucosyloxy, maltosyloxy, cellobiosyloxy, lactosyloxy, maltotriosyloxy, maltotetraosyloxy, maltopentaosyloxy, maltohexaosyloxy, maltoheptaosyloxy, and sialosyloxy, and in this case, at least one of R$_{10}$, R$_{11}$, R$_{12}$, and R$_{13}$ is glycosyloxy group as defined above.

2. A composition comprising at least one of the glycosides of catechol estrogen of claim 1 in a lipid peroxidation suppressing amount and a pharmaceutically acceptable carrier.

* * * * *